(12) United States Patent
Martinson et al.

(10) Patent No.: US 10,383,552 B2
(45) Date of Patent: Aug. 20, 2019

(54) GAIT ANALYSIS MEDICAL ASSISTANCE ROBOT

(71) Applicant: TOYOTA JIDOSHA KABUSHIKI KAISHA, Toyota-shi, Aichi-ken (JP)

(72) Inventors: Eric Martinson, Mountain View, CA (US); Peter Cottrell, Mountain View, CA (US)

(73) Assignee: TOYOTA JIDOSHA KABUSHIKI KAISHA, Toyota-shi (JP)

( * ) Notice: Subject to any disclaimer, the term of this patent is extended or adjusted under 35 U.S.C. 154(b) by 516 days.

(21) Appl. No.: 15/139,275

(22) Filed: Apr. 26, 2016

(65) Prior Publication Data

US 2017/0303825 A1 Oct. 26, 2017

(51) Int. Cl.
*A61B 5/00* (2006.01)
*A61B 5/11* (2006.01)

(52) U.S. Cl.
CPC ............ *A61B 5/112* (2013.01); *A61B 5/0077* (2013.01); *A61B 5/7282* (2013.01); *A61B 5/0046* (2013.01); *Y10S 901/01* (2013.01)

(58) Field of Classification Search
CPC ..... A61B 5/0077; A61B 5/112; A61B 5/7282; Y10S 901/01; Y10S 901/46
See application file for complete search history.

(56) References Cited

U.S. PATENT DOCUMENTS

| | | | |
|---|---|---|---|
| 7,158,859 B2* | 1/2007 | Wang ..................... | B25J 5/007 318/568.11 |
| 7,243,024 B2* | 7/2007 | Endicott ................ | G01C 21/20 340/995.16 |
| 8,002,672 B2 | 8/2011 | Brunner | |
| 8,744,664 B2* | 6/2014 | Day ..................... | G05D 1/0278 701/25 |
| 9,427,863 B2* | 8/2016 | Lee ....................... | B25J 9/0003 |
| 9,511,495 B2* | 12/2016 | Shetty ................... | B25J 9/1697 |
| 9,586,316 B1* | 3/2017 | Swilling ............... | B25J 9/1664 |

(Continued)

FOREIGN PATENT DOCUMENTS

| | | |
|---|---|---|
| JP | 2006048666 A | 2/2006 |
| JP | 2015109937 A | 6/2015 |

(Continued)

OTHER PUBLICATIONS

Adachi, Hiroyuki et al., "Walking data acquisition using KINECT mounting robot," 2014, vol. 114, 25-30, pp. 1-8 (with JP Office Action's Partial Translation).

(Continued)

*Primary Examiner* — Sean P Dougherty
(74) *Attorney, Agent, or Firm* — Patent Law Works LLP

(57) ABSTRACT

This disclosure describes, according to some implementations, a system and method for capturing sensor data for gait analysis of a subject using a robot. In an example method, a robot unit receives an instruction to monitor a gait of a subject; initializes a monitoring approach in response to receiving the instructions to begin monitoring the gait of the subject; collecting sensor data capturing movement of the subject along the pathway portion; and generating gait data for gait analysis based on the sensor data. In various embodiments, the monitoring approaches may include an active approach, a passive approach, or a hybrid approach.

20 Claims, 10 Drawing Sheets

(56) References Cited

U.S. PATENT DOCUMENTS

| | | | |
|---|---|---|---|
| 2006/0064203 | A1 | 3/2006 | Goto et al. |
| 2008/0108913 | A1 | 5/2008 | Lengsfeld et al. |
| 2009/0030350 | A1 | 1/2009 | Yang et al. |
| 2015/0324637 | A1 | 11/2015 | Utsunomiya et al. |
| 2017/0116869 | A1* | 4/2017 | Pape .................... A61H 1/0262 |
| 2018/0289579 | A1* | 10/2018 | Agrawal ................ A61H 3/008 |

FOREIGN PATENT DOCUMENTS

| | | | |
|---|---|---|---|
| JP | 2016073630 A | 5/2016 | |
| JP | 2017196414 A | * 11/2017 | ........... A61B 5/0077 |

OTHER PUBLICATIONS

Iida, Masahiro et al., "A Study on Chasing Algorithm and Walking Parameters Acquisition Using Home Robot," AIJ J. Technol. Des. vol. 22, No. 50, 253-257, Feb. 2016, pp. 1-6 (with JP Office Action's Partial Translation).

Gabel et al., "Full Body Gait Analysis with Kinect," IEEE International Conference on Engineering in Medicine and Biology Society, 2012 (4 pages).

El-Yacoubi et al., "HMM-based Gait Modeling and Recognition under different Walking Scenarios," IEEE International Conference on Multimedia Computing and Systems, 2011 (5 pages).

Stone et al., "Unobtrusive, Continuous, In-Home Gait Measurement Using the Microsoft Kinect," IEEE Transactions on Biomedical Engineering, Oct. 2013 (8 pages).

Wikipedia, "Gait Analysis," download from https://en.wikipedia.org/wiki/Gait_analysis Mar. 23, 2016 (6 pages).

* cited by examiner

GAIT ANALYSIS MEDICAL ASSISTANCE ROBOT

BACKGROUND

The specification relates to gait analysis of a human by a robot unit.

Studies have shown that human gait is an important indicator of health, indicative of diabetes, neurological conditions, or fall predictions. Gait analysis generally requires similar conditions be reproduced in order to compare newly measured data with a previously determined baseline condition. Similar conditions are often captured in a clinical environment. A typical clinical environment may have one or more cameras placed around a walkway or treadmill, where the camera(s) and treadmill (if applicable) are coupled to and controlled by a computer. For improved accuracy, the camera position(s) may be substantially the same (e.g., have a stationary side view on of a subject on a treadmill, similar camera views of the subject along different portions of the walkway, etc.). The actual or simulated pathway is made long enough (e.g., ten feet) for a complete gait analysis to be performed on the target subject. Knowing the camera position and the length of the path allows for the reliable identification of medical issues related to the subject's movement.

While these types of controlled clinical environments for measuring gait may be functional, they have significant disadvantages. These types of clinical environments are generally restrictive because they require patrons, who are not all equipped or in suitable health, to go through the hassle of scheduling appointments and make dedicated trips to a clinical facility. These types of clinical environments are also expensive, as they require cleaning, maintenance, and specialized training and staffing by medical professionals.

Some treadmill-based setups may be installed and used by a target subject at home, such as the approach described by U.S. Pat. No. 8,002,672. This approach uses pressure sensors mounted to a treadmill to capture data. However, as with a clinical environment, a treadmill is inherently stationary and therefore the target subject is limited to having his/her gait analyzed in a single location (i.e., the treadmill and sensor configuration cannot be used to analyze gait in multiple locations). While it is possible for the pressure sensors to be mounted on other surfaces, such as a sidewalk, the cost of equipping a large environment is likely prohibitive to being able to gather data throughout the environment.

Some approaches use sensors mounted on the body of the subject to capture gait data. For example, U.S. Patent Application No. 2009/0030350 describes affixing an accelerometer to the subject for continuous gait analysis, and U.S. Patent Application No. 2008/0108913 describes mounting pressure sensors to shoes to analyze gait and detect falls of the subject. However, these types of wearable sensors have at least two significant drawbacks. First, subjects may dislike wearing the sensor, or simply forget to attach the sensor. Second, positioning the sensor repeatedly (e.g., day to day) during wear in a consistent manner is difficult to replicate. Further, while affixing the wearable device to clothing may help in overcoming the two issues discussed above, affixing the wearable device to clothing increases noise in the resulting data. Further, it can restrict the manner in which the equipped clothing can be handled and washed.

Some approaches utilize 3D cameras mounted in an environment to monitor subjects and capture gait data. For example, E. Stone and M. Skubic, "Unobtrusive, Continuous, In-Home Gait Measurement Using the Microsoft Kinect," *IEEE Transactions on Biomedical Engineering*, vol. 60, no. 10, pp. 2925-2932, 2013 (Stone), describes a Microsoft Kinect™ skeletal tracker, which uses RGB-D sensors affixed to the ceilings of a target subject's home, to perform long-term gait monitoring of the target subject over a period of months. While this approach demonstrates that subjects could be recognized using the data gathered by the RGB-D sensors, the single camera placement restricted the amount of environments that could be monitored. In particular, only the rooms equipped with the tracker can be monitored, and as a result, the tracker is unable to monitor the health and activity of the target subject in other environments.

Some approaches capture gait data from multiple camera positions and/or angles. For example, M. Gabel, R. Gilad-Bachrach, E. Renshaw, and A. Schuster, "Full Body Gait Analysis with Kinect," in the proceedings of the International Conference of the IEEE EM BS, San Diego Calif. USA, Aug. 28, 2000-Sep. 1, 2000 ("Gabel"), describes using an algorithm that recognizes people under a variety of camera angles. In particular, the algorithm uses the Microsoft Kinect™ skeletal tracker to recognize people under varied camera angles, including conditions where the gait was learned on one camera angle, and then evaluated on a separate camera angle. Gabel's approach disadvantageously requires full visibility of the subject and an unobstructed view from the camera in order to acceptably perform. Additionally, Gabel's approach exhibited degradation as the camera angle changed.

Some approaches use thermal image cameras to measure the gait of a target subject. For example, M. El-Yacoubi, A. Shaiek and B. Dorizzi, "HMM-based gait modeling and recognition under different walking scenarios," 2011 *International Conference on Multimedia Computing and Systems*, 2011, describes using thermal imagery and Hidden Markov Models to extract silhouettes to model the gait of the subject. While, once trained, this approach can recognize various walking conditions of a target subject, it is focused on recognition and does not provide significant contributions to gait data collection or analysis methods.

Therefore, accessible and flexible technology is needed that is capable of monitoring the gait of a subject engaged in a variety of different activities and/or environments.

SUMMARY

The specification overcomes the deficiencies and limitations of the solutions described in the Background section at least in part by providing novel technology for performing gait analysis using a robot unit.

According to one innovative aspect of the subject matter described in this disclosure, a system includes one or more computer processors and one or more memories storing instructions that when executed by the one or more processors, cause the system to perform operations including: receiving an instruction to monitor a gait of a subject, initializing a monitoring approach in response to receiving the instructions to begin monitoring the gait of the subject, collecting sensor data capturing movement of the subject along a pathway portion, and generating gait data for gait analysis based on the sensor data.

In general, another innovative aspect of the subject matter described in this disclosure may be embodied in methods that include receiving, using one or more computer processors, an instruction to monitor a gait of a subject; initializing, using the one or more computer processors, a monitoring approach in response to receiving the instruction to begin monitoring the gait of the subject; collecting, based on the monitoring approach and using the one or more sensors coupled to the one or more computer processors, sensor data capturing movement of the subject along a pathway portion; and generating gait data for gait analysis based on the sensor data.

In general, another innovative aspect of the subject matter described in this disclosure may be embodied in methods that include receiving, using one or more computer processors, an instruction for a robot unit to monitor a gait of a subject; determining, using the one or more computer processors, a pathway portion that the subject is to move along; determining, using the one or more computer processors, a position from which the one or more sensors of the robot unit can view the pathway portion; actuating one or more actuators of the robot unit to move the robot unit to the position; capturing, using the one or more sensors of the robot unit, sensor data of the subject moving along the pathway portion; and generating, using the one or more processors, gait data using the sensor data.

Other aspects include corresponding methods, systems, apparatus, and computer program products for these and other innovative aspects.

These and other implementations may each optionally include one or more of the following features and/or operations. For instance, the features and/or operations include: providing, using an output device coupled to the one or more computer processors, a notification to the subject that sensor data for gait analysis will be captured; determining, using the one or more computer processors, the pathway portion; determining, using the one or more computer processors, a position of the one or more sensors for capturing the sensor data; providing, using the one or more computer processors, a signal to move the one or more sensors to the position; providing, using the one or more computer processors, a first guidance to the subject to begin moving along the pathway portion; capturing, using the one or more sensors, the sensor data; that the monitoring approach is a passive monitoring approach, the sensor data includes surroundings data, subject data, and position data; that collecting sensor data includes collecting the sensor data using the passive monitoring approach by capturing, using the one or more sensors, the sensor data, determining, using the one or more computer processors, that the surroundings data, subject data, and position data included in the sensor data meet passive monitoring approach conditions, and generating the gait data using the sensor data responsive to the passive monitoring approach conditions being met; that the passive monitoring conditions include a pre-determined length of a pathway, a stable position for viewing the pathway, and image data of the subject moving along the pathway; that the monitoring approach is a hybrid approach; that collecting sensor data includes collecting sensor data using the hybrid approach by capturing, using the one or more sensors, first sensor data including surroundings data, subject data, and position data, determining, using the one or more computer processors, that hybrid data conditions have been met based on the sensor data, determining, using the one or more computer processors, the pathway portion of the subject based on the sensor data, determining, using the one or more computer processors, a position of the one or more sensors, that provides the one or more sensors with a view of the pathway portion, providing, using the one or more computer processors, a signal to move the one or more sensors to the position, and capturing, using the one or more computer processors, second sensor data of the subject moving along the pathway portion; that determining that the hybrid data conditions have been met further comprises determining, using the one or more processors, a potential pathway of the subject that exceeds a pre-defined length in the data; predicting, using the one or more processors, that the subject will move along the potential pathway within a period, using the data; that collecting sensor data further comprises determining, using the one or more computer processors, a first pathway including the pathway portion for the subject and a second pathway parallel to the first pathway for monitoring the gait of the subject, and capturing, using the one or more computer processors, the sensor data by moving along the second pathway parallel to the subject as the subject moves along the first pathway; and modifying, using the one or more computer processors, the sensor data to account for motion anomalies.

The technology disclosed herein is particularly advantageous in a number of respects. For instance, by using performing continuous passive observation of the subject in a home environment, a robot unit can provide continuous health monitoring in many cases without time or location constraints, leading to personalized, convenient treatment, quicker results, and better overall care. Additionally, a robot unit may be deployed in the subject's natural environment to monitor the gait data of the subject, resulting in a less expensive and more convenient means of gathering gait data compared to a clinical laboratory. In some cases, body-mounted sensors may be omitted, leading or a more natural behavior by the subject (because the subject is less focused on their movement, more at ease, etc.), which may ultimately provide more accurate gait data. Further, not having to position the robot manually provides for better quality observations compared with randomly placed environmental sensors or manually operated devices. It should be understood that the foregoing advantages are provided by way of example and that the technology may have numerous other advantages and benefits. Further, it should be understood that the Summary describes various example aspects of the subject matter of this disclosure and is not intended to encompass every inventive aspect.

BRIEF DESCRIPTION OF THE DRAWINGS

The specification is illustrated by way of example, and not by way of limitation in the figures of the accompanying drawings in which like reference numerals are used to refer to similar elements.

DETAILED DESCRIPTION

Figure 1:
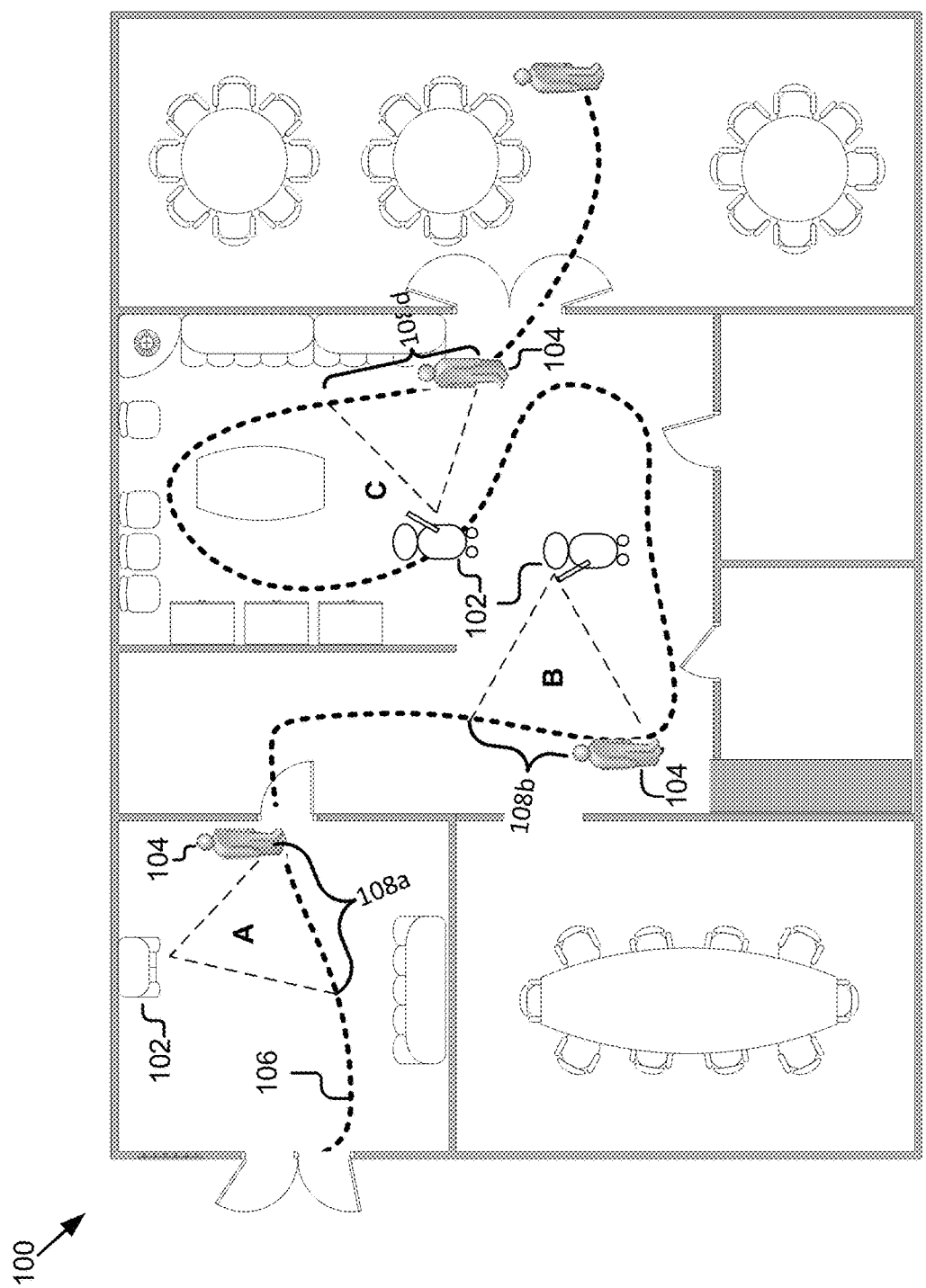
FIG. 1 is a high-level diagram illustrating a robot unit performing gait analysis.

This document discloses technology for performing gait analysis using a robot unit. FIG. 1 illustrates a diagram of a robot unit 102 performing gait analysis on a subject 104. The diagram illustrates a top-level view of an example environment 100 and a pathway 106 illustrating where the subject 104 has been observed by the robot unit 102 moving through the environment 100. In some implementations, the environment 100 may include various rooms that the subject 104 may move through and/or various objects (e.g., furniture, tools, room specific items, etc.) that the subject 104 may move around as illustrated by the pathway 106. The pathway 106 is an illustrative example of where in the environment 100 the subject 104 can move over a period of time.

The robot unit 102 may be instructed to monitor the subject 104 as the subject 104 moves through the environment 100. The robot unit 102 may be capable of moving and navigating through the environment 100 as the robot unit 102 monitors the subject 104. In some implementations, the robot unit 102 may be a medical assistance robot programmed to provide various types of medical assistance to the subject 104, such as monitoring of the subject 104, alerting medical professionals in the event of an emergency, and/or capturing data of the subject 104 performing various tasks in different environments. Using the medical assistance robot, a doctor may be able to monitor the subject 104 in other environments outside of when the subject 104 is in the doctor's office or a clinical environment (e.g., the robot unit 102 may be programmed to monitor the subject 104 in the subject 104's home or work environment). By having the robot unit 102 monitor the subject 104 in different environments and/or settings, the doctor may be able to insure using captured data that the subject 104 is performing various therapies correctly in those various environments.

The robot unit 102 is programmed to capture sensor data using sensor(s) 204 while monitoring a target subject 104, and generate gait data using the sensor data. Gait data includes data describing locomotion characteristics of a target subject 104 as the target subject moves through a defined portion of a pathway 106. Gait data may include image sequences depicting the target subject 104 at different points in time and locations along the pathway 106 portion. Gait data may include position, movement, and/or trajectory data of the target subject 104's joints, torso, legs, arms, other appendages, etc., at different points in time and locations along the pathway 106 portion; the length of the pathway 106 portion; a timestamp and/or location for each sensor data point (e.g., each image frame); the relative position of the sensor(s) relative to a known position of the target subject 104; the overall time take by the target subject 104 to navigate the pathway 106 portion, etc. Further example locomotion characteristics described by the gait data may include movement and speed of the subject 104, stride length of the subject 104, time for subject 104 to move a given distance, amount of steps taken by the subject 104 to move that distance, differences between left and right steps of the subject 104, posture of subject 104, etc.

A target subject's 104 pathway generally includes one or more portions that are suitable for performing gait analysis. For example, the pathway 106 depicted in FIG. 1 includes portions A, B, and C that meets gait criteria for capturing gait data. These gait criteria may include, but are not limited to, a pathway 106 portion length parameter (e.g., ten feet, ten meters, an alternative pre-defined distance that is capable of capturing sufficient data for gait analysis, etc.), a pathway 106 portion straightness tolerance (e.g., 0-5% deviation from completely straight line), and clearance from obstructions that could prevent sensor(s) 204 from capturing requisite data. In some cases, data from two or more portions A, B, and/or C may be combined if the length of each portion is not long enough individually for a complete gait analysis but their combined length is.

Depending on the approach, a robot unit 102 may dynamically and/or autonomously identify one or more of the portions A, B, and C, based on a determination by the programming of the robot unit 102 that each portion, or a combination of portions, satisfies the gait criteria. Alternatively or additionally, a stakeholder, such as a technician, physician, or the target subject 104, may input one or more of the portions A, B, and C.

The robot unit 102 may position itself to have camera poses capable of monitoring the portions A, B, and/or C of the pathway 106. The camera pose positions the robot unit 102 a sufficient distance from the target subject 104 at each of the different locations A, B, and C for the robot unit 102 to capture the sensor data. More specifically, the location of each pose allows the sensor(s) 204 to capture the movement of the subject along the length of the pathway portion 106 from a start point to an end point of the pathway portion. The lengths of each pathway 106 portion A, B, and C are respectively labeled as 108a, 108b, and 108c.

The robot unit 102 may be programmed to use various approaches to identify the pathway 106 and/or the camera pose 108 and capture sensor data of the subject 104. In an active approach, the robot unit 102 may indicate to the subject 104 when to start and stop movement (e.g., walking), and may capture and process sensor data as the subject 104 follows those instructions. In some implementations, the robot unit 102 may also direct the user 104 to and/or along the pathway 106 by providing signals via various output devices (audio instruction, displaying instructions on a screen included in or coupled to the robot unit 102, etc.).

In a passive approach, the robot unit 102 passively monitors the subject 104 as the subject 104 moves through the environment 100. Sensor data captured as part of the monitoring process may be analyzed to determine if it is suitable for gait analysis (e.g., meets the gait criteria discussed herein), and if so, may be processed and/or provided as gait data. The passive approach allows the robot unit 102 to perform gait analysis without interrupting the subject 104 or indicating to the user that gait analysis is being performed. Often times, interruptions or indications may cause the subject 104 to be more conscious of their movement, and react by changing aspects of their performance (e.g., posture, etc.). As such, a passive approach can be beneficial because it can capture gait data reflecting a subject 104's natural movement.

In a hybrid approach, the robot unit 102 identifies, in advance, when conditions will likely be met for capturing sensor data, and the robot unit 102 pre-positions itself accordingly. In some implementations, the robot unit 102 may estimate or determine the subject 104's intended destination in advance, and then determine where to position itself to capture sensor data of the subject 104 while moving toward that destination, as discussed elsewhere herein.

Figure 2:
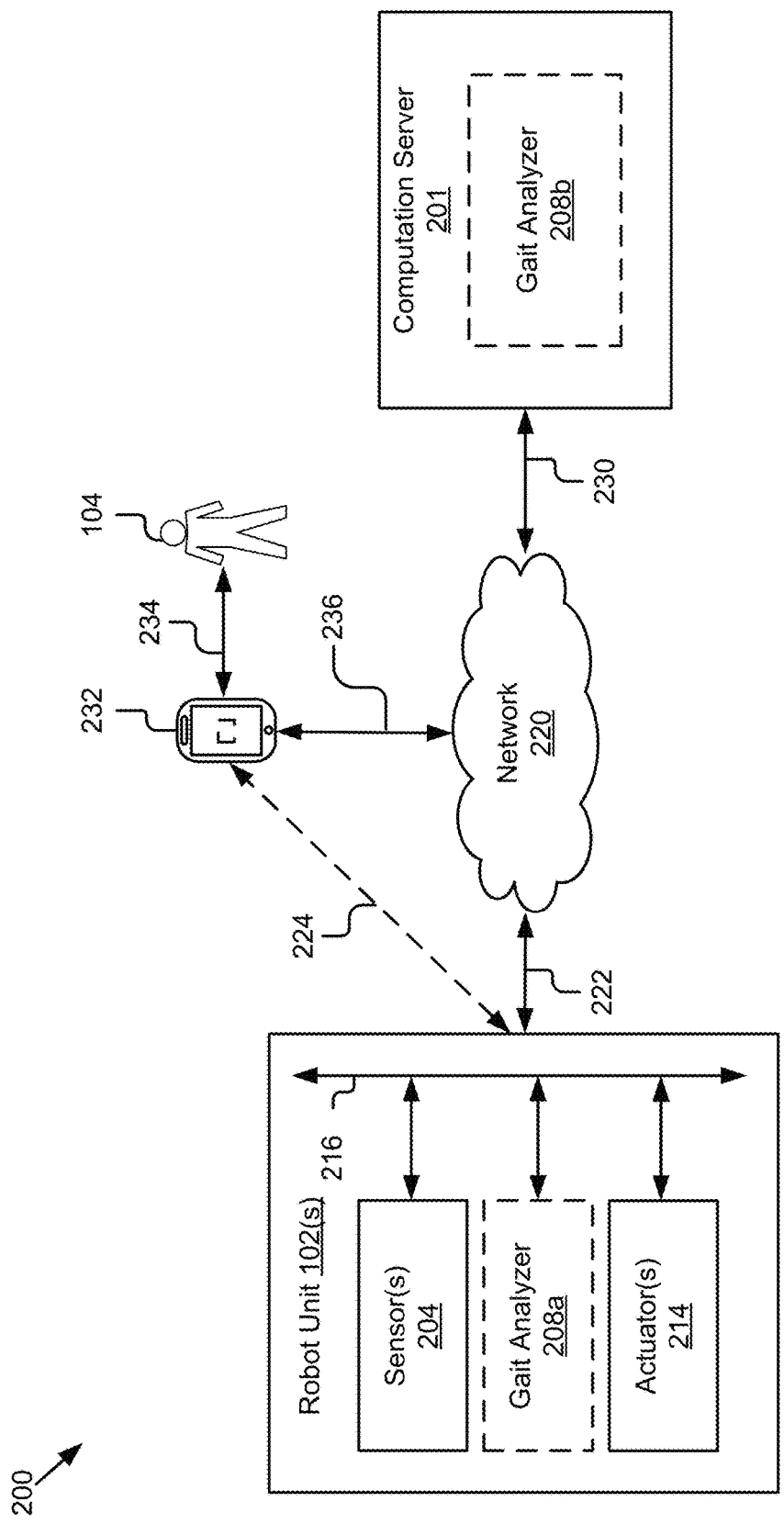
FIG. 2 is a block diagram illustrating an example gait analysis system.

FIG. 2 illustrates a gait analysis system 200. The system 200 may include any number of robot unit(s) 102. A robot unit 102 may be wirelessly coupled to a network 220 for communication with the other entities of the system 200 as reflected by signal line 222. The system 200 may further include one or more client device(s) 232, which may be communicatively coupled to the network 220, as reflected by signal line 236. In some implementations, the client device 232 may additionally and/or alternatively be coupled directly to the robot unit 102 via signal line 224, such as via a wireless and/or wired connection. Subject 104 may be a human moving through an environment, and the subject 104 may interact with the client device 232 via input and output devices, as reflected by line 234. In some implementations, additional and/or alternative users (e.g., a doctor, a technician, etc.) may interact with the client device 232 via input and output devices to provide remote commands, and receive gait data from the robot unit 102 (e.g., on the client device 232 via the network 220), etc. The system 200 may further include a computation server 201, which may be communicatively coupled to the network 220, as reflected by signal line 230.

The robot unit 102 may include one or more sensor(s) 204, an instance of the gait analyzer 208 (labeled 208a), and one or more actuator(s) 214. The sensor(s) 204, the gait analyzer 208a, and the actuator(s) 214 may be coupled together by a communication bus 216. It should be understood that the robot unit 102 may include additional and/or fewer components, such as an operating system, other software, input and/or output device, actuator controllers, housings, other mechanical and/or electrical components often used in robotics, etc.

The sensor(s) 204 may include one or more sensors configured to capture signals (e.g., light, radio waves, sound waves, etc.) from the surrounding environment and to generate and/or processes sensor data therefrom. For instance the sensor(s) 204 may include a range camera, such as but not limited to an RGB-D camera, a stereo camera, a structured light camera/scanner, time-of-flight camera, interferometer, modulation imager, a laser rangefinder, a light-field camera, an intensified CCD camera, etc., although it should be understood that other types of sensors may be used, such as but not limited to an ultrasound sensor, a color camera, an infrared camera, etc. In some implementations, the sensor(s) 204 may include a combination of different types of sensors, such as accelerometers, gyroscopes, thermometers, barometers, thermocouples, microphones, or other conventional sensing devices. Kinect sensor by Microsoft, various stereo vision systems, etc., are further non-limiting examples of cameras that the sensor(s) 204 may include. The sensor(s) 204 may be incorporated into the robot unit 102 or may be a disparate device that is coupled thereto via a wireless or wired connection.

In various implementations, the sensor(s) 204 may generate and send the sensor data (e.g., image data, audio data, and/or depth data describing objects in the environment) to the robot unit 102 and/or the computation server 101 for processing, as described elsewhere herein.

The gait analyzer 208, reflected in FIG. 2 as instances 208a and/or 208b, may be operable to capture and/or analyze sensor data of the subject 104, and generate, store, and/provide gait data. The gait analyzer 208 is discussed in further detail elsewhere herein, such as with reference to at least FIGS. 3A-6.

The actuator(s) 214 include mechanical and/or electrical devices that are capable of converting energy into motion. The actuator(s) 214 may be electric, pneumatic, hydraulic, magnetic, mechanical, and/or magnetic, and/or a combination of the foregoing. Non-limiting example actuator(s) 214 include electric motors, servomechanism, hydraulic cylinders, pneumatic actuators, corresponding gearing, connectors, and kinematic components, etc. The actuator(s) 214 may include an actuator controller for controlling the actuator(s) 214 of the robot unit 102. For example, the actuator controller may send signals (e.g., motion commands, calibration commands, etc.) to the actuator(s) 214 to control the movement or state of the robot unit 102, including the direction and speed of the robot unit 102 itself and/or its appendages and components. The actuator controller may be comprised of hardware, software, and/or a combination of the foregoing. For example, the actuator controller may comprise standard computer circuitry, firmware, etc., for controlling actuator(s) 214. In some implementations, the actuator controller may be integrated with a processor, such as processor(s) 302 depicted in FIG. 2A, or may be distinct from but coupled to the processor(s) 302 via the bus 216.

The components of the robot unit 102 are communicatively coupled via the bus 216, which is discussed in further detail with reference to at least FIG. 3A.

The computation server 201 includes computer hardware and software having data processing, storing, and communication capabilities, as discussed elsewhere herein. For example, the computation server 201 may include one or more hardware servers, server arrays, storage devices and/or systems, etc. In some implementations, the computational server 201 may include one or more virtual servers, which operate in a host server environment. As depicted, the computation server 201 may include an instance of the gait analyzer 208, labeled 208b, which is discussed in further detail elsewhere herein.

Figure 3A:
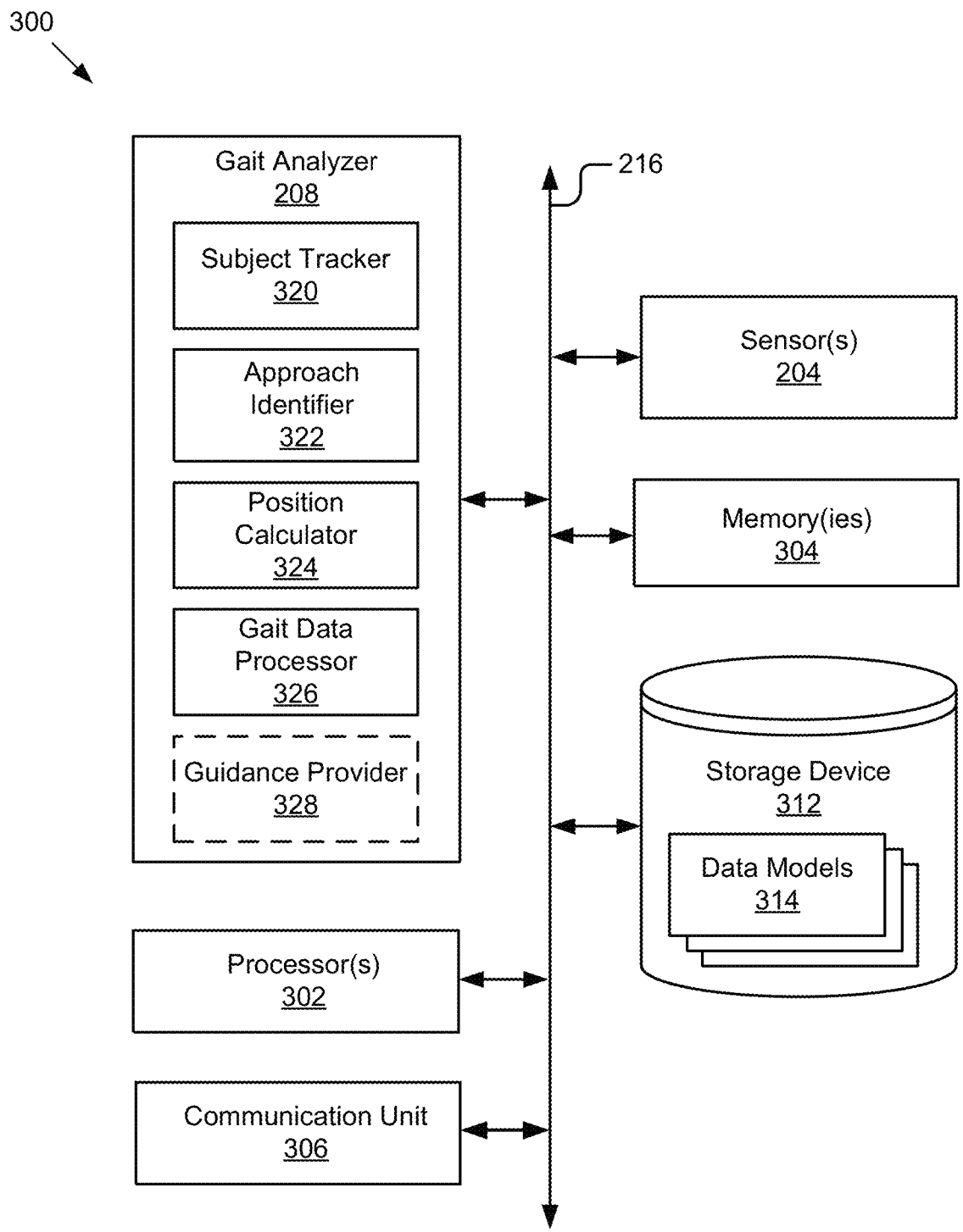
FIG. 3A is a block diagram of an example computing device.

FIG. 3A is a block diagram of an example computing device 300. As depicted, the computing device 300 may include processor(s) 302, memory(ies) 304, a communication unit 306, sensor(s) 204, a gait analyzer 208, and/or a storage device 312, which may be communicatively coupled by a standard communication bus 216. The computing device 300 depicted in FIG. 3A is provided as an example and it should be understood that it may take other forms and include additional or fewer components without departing from the scope of the present disclosure, such as the components of the robot unit 102 depicted in FIG. 2 (e.g., if reflecting the architecture of a robot unit 102), standard input and output devices (e.g., pointer devices, keyboards, displays, cameras, microphones, etc.) for inputting commands, human-computer interaction, and/or receiving notifications, etc., and/or any other suitable electrical and/or mechanical components, etc.

The processor(s) 302 may execute instructions by performing various input/output operations, logical operations, and/or mathematical operations. The processor(s) 302 may have various known computing architectures to process data signals. The processor(s) 302 may be physical and/or virtual, and may include a single processing unit or a plurality of processing units. In some implementations, the processor(s) 302 may be capable of generating and providing electronic display signals to a display device (not shown), supporting the display of images, capturing and transmitting images, performing complex tasks including various types of feature extraction and sampling, etc. In some implementations, the processor(s) 302 may be coupled to the memory(ies) 304 via the bus 216 to access data and instructions therefrom and store data therein. The bus 216 may couple the processor(s) 302 to one or more other components including, for example, the memory(ies) 304, the sensor(s) 204, the communication unit 306, the storage device 312, the gait analyzer 208, etc. It should be understood that the processor(s) 302 may be a single device or may include multiple types of devices and configurations.

The memory(ies) 304 may store and provide access to data to the other components of the computing device 300. In some implementations, the memory(ies) 304 may store instructions and/or data that may be executed by the processor(s) 302. For instance, the memory(ies) 304 may store the gait analyzer 208 and/or components thereof. The memory(ies) 304 may also be capable of storing other instructions and data, including, for example, an operating system, hardware drivers, other software applications, databases, etc. The memory(ies) 304 may be coupled to the bus

216 for communication with the processor(s) 302 and the other components of the computing device 300.

The memory(ies) 304 may include one or more non-transitory computer-usable (e.g., readable, writeable, etc.) media, which may include an apparatus or device that can contain, store, communicate, propagate or transport instructions, data, computer programs, software, code, routines, etc., for processing by or in connection with the processor(s) 302. In some implementations, the memory(ies) 304 may include one or more of volatile memory and non-volatile memory. For example, the memory(ies) 304 may include, but is not limited, to one or more of a dynamic random access memory (DRAM) device, a static random access memory (SRAM) device, a discrete memory device (e.g., a PROM, FPROM, ROM), a hard disk drive, an optical disk drive (CD, DVD, Blue-ray™, etc.). It should be understood that the memory(ies) 304 may be a single device or may include multiple types of devices and configurations.

The communication unit 306 may include one or more interface devices for wired and/or wireless connectivity with the network 220, as reflected by signal line 222, and the other components of the system 200. For instance, the communication unit 306 may include, but is not limited to, wireless transceivers for sending and receiving signals using Wi-Fi™; Bluetooth®, near-field communication (NFC), cellular communications, etc.; CAT-type interfaces; USB interfaces; geolocations sensors (e.g., GPS transceivers); various combinations thereof; etc. The communication unit 306 may be coupled to the other components of the computing device 300 via the bus 216. The communication unit 306 may communicate using various standard communication protocols, including, for example, those discussed elsewhere herein.

The bus 216 may include a communication bus for transferring data between components of a computing system or between computing systems, a network bus system including the network 202 and/or portions thereof, a processor mesh, a combination thereof, etc. In some implementations, the bus 216 may represent one or more buses including an industry standard architecture (ISA) bus, a peripheral component interconnect (PCI) bus, a universal serial bus (USB), or some other bus known to provide similar functionality. Additionally and/or alternatively, the various components of the computing device 300 may cooperate and communicate via a software communication mechanism implemented in association with the bus 216. The software communication mechanism may include and/or facilitate, for example, inter-process communication, local function or procedure calls, remote procedure calls, an object broker (e.g., CORBA), direct socket communication (e.g., TCP/IP sockets) among software modules, UDP broadcasts and receipts, HTTP connections, etc. Further, any or all of the communication could be secure (e.g., SSH, HTTPS, etc.).

The storage device 312 is an information source for storing and providing access to data. The data stored by the storage device 312 may be organized and queried using various criteria including organizing into data models 314. The data models 314 may include data and algorithms for analyzing gait data, for example, the data models may include previous gait data of a specific subject 104, model gait patterns, environment and/or object recognition data, etc. These models may be predetermined, or determined and/or further learned by the gait analyzer 208. Examples of the types of data stored by the storage device 312 as data models 314 may include data tables, databases, or other organized collections of data discussed elsewhere herein.

The storage device 312 may be included in the robot unit 102 or in another computing system and/or storage system distinct from but coupled to or accessible by the robot unit 102. The storage device 312 may include one or more non-transitory computer-readable media for storing the data. In some implementations, the storage device 312 may be incorporated with the memory(ies) 304 or may be distinct therefrom. In some implementations, the storage device 312 may store data associated with a database management system (DBMS) operable on the robot unit 102. For example, the DBMS could include a structured query language (SQL) DBMS, a NoSQL DMBS, a file system, flat files, various combinations thereof, etc. In some instances, the DBMS may store data in multi-dimensional tables comprised of rows and columns, and manipulate, e.g., insert, query, update and/or delete, rows of data using programmatic operations.

The gait analyzer 208 includes computer logic executable to gather sensor data, perform gait analysis, and/or generate and provide gait data. The computer logic may be implemented in software, hardware, and/or a combination of the foregoing as one with skill in the art would understand. For example, the gait analyzer 208 may program the processor(s) 302 to perform the operations discussed herein. For instance, the gait analyzer 208's software routines may be stored in the memory(ies) 304, and retrieved and executed by the processor(s) 302. In another example, the gait analyzer 208 may include circuitry implemented by the processor(s) 302 to perform the acts and/or functionality discussed herein. Non-limiting examples of circuitry include a field-programmable gate array (FPGA), an application-specific integrated circuit (ASIC), wiring, standard electronic components, boards, and/or other suitable circuitry, etc.

This document sometimes refers to the gait analyzer 208, and/or its subcomponents, as the actor (in the third person) for convenience and so as not to obscure the various operations carried out by them. However, it should be understood that these elements are logic executable by the processor(s) 302, program the processor(s) 302, etc., to perform the specific operations described herein.

As depicted in FIG. 2A, the gait analyzer 208 may include various subcomponents, such as a subject tracker 320, an approach identifier 322, a position calculator 324, a gait data processor 326, and/or a guidance provider 328, although it should be understand that one or more of these components may take different forms, may be consolidated together and/or divided into further components, without departing from the scope of this disclosure. The gait analyzer 208 depicted in FIG. 3A is provided as an example and it should be understand that it may take other forms and include additional or fewer components without departing from the scope of the present disclosure. For instance, in some configurations, the gait analyzer 208, or various aspects thereof, may be distributed over the network 220 on disparate devices in disparate locations or all the functionality of the gait analyzer 208 may be resident code operable by a single computing device or group of related devices. Other configurations are also possible and contemplated. Each of these components 320, 322, 324, 326, and 328 may be coupled to the storage device 312 and/or memory(ies) 314 to store and retrieve data such as approach data, sensor data, pathway data, and/or gait data.

The subject tracker 320 includes computer logic operable to track a subject 104 as the subject 104 moves through the environment. In some implementations, tracking a subject 104 may include performing scene and/or image recognition from sensor(s) 204 and providing instructions to navigate the robot unit 104 to follow the subject 104 as discussed elsewhere herein. In further implementations, tracking the subject 104 includes determining pathways in the environment that the subject 104 may move along as discussed elsewhere herein. In an example, the subject tracker 320 may send an instruction to the actuator(s) 214 of the robot unit 102 to follow a subject 104 as the subject moves down a hallway and into a room. In a further example, the subject tracker 320 may determine that the hallway the subject 104 may move down meets criteria for determining a future pathway.

The subject tracker 320 may be coupled to the approach identifier 322, position calculator 324, and/or gait data processor 326 to provide information on potential pathways and/or receive locations on where to move the robot unit 102. By way of example, the subject tracker 320 may be executed by making a procedure call, calling an object-oriented method, or invoking another suitable process. For instance, a main program of the gait analyzer 208, the approach identifier 322, gait data processor 326, an external or internal API, or another component, may instantiate the subject tracker 320, although other execution paths are also applicable and contemplated.

In some implementations, the subject tracker 320 is adapted for cooperation and communication with the processor(s) 302, the memory(ies) 304 and other components of the example computing device 300 via the bus 216. The subject tracker 320 may store data and commands received while monitoring the subject 320 in the memory(ies) 304 and/or storage device 312. The subject tracker 320 may be coupled to output device(s) to output information to a subject 104 and/or other objects in the surroundings. The subject tracker 320 may be coupled to input device(s) to receive information from a subject 104 and/or other objects in the surroundings. The subject tracker 320 may be coupled to the actuator controller for controlling the actuator(s) 214 as discussed elsewhere, herein. The subject tracker 320 may include a route calculator 350 as described with reference to at least FIG. 3B.

The approach identifier 322 includes computer logic operable to determine whether to use an active, passive, and/or hybrid approach for collecting sensor data for gait analysis. In some implementations, determining an approach may include analyzing data received from sensor(s) 204 and performing scene and/or image recognition to determine whether conditions for a particular approach are met, as discussed elsewhere herein. In an example, the approach identifier 322 may receive sensor data from the sensor(s) 204 indicating that the subject 104 is moving down a hallway that has been predetermined to be a pathway for capturing sensor data and the approach identifier 320 may use this condition to select to use a hybrid approach. The approach identifier 322 may be coupled to the gait data processor 326 to provide approach data on which approach for the gait data processor 326 to use to capture sensor data. The approach data may include data identifying which conditions are met and which approach to use. By way of example, the approach identifier 322 may be executed by making a procedure call, calling an object-oriented method, or invoking another suitable process. For instance, a main program of the gait analyzer 208, gait data processor 326, an external or internal API, or another component, may instantiate the approach identifier 322, although other execution paths are also applicable and contemplated.

In some implementations, the approach identifier 322 is adapted for cooperation and communication with the processor(s) 302, the memory(ies) 304 and other components of the example computing device 300 via the bus 216. The approach identifier 322 may store data and commands received related to the determination of which approach to use in the memory(ies) 304 and/or storage device 312. The approach identifier 322 may be coupled to output device(s) to output information to a subject 104 and/or other objects in the surroundings. The approach identifier 322 may be coupled to input device(s) to receive information from a subject 104 and/or other objects in the surroundings. The approach identifier 322 may include one or more specific approach identifiers as described with reference to at least FIG. 3C.

The position calculator 324 includes computer logic operable to determine a position to capture sensor data by the robot unit 102 and/or sensor(s) 204. In some implementations, determining a position to capture sensor data may include analyzing data received from sensor(s) 204 and performing scene and/or image recognition to determine a position appropriate for capturing sensor data, as discussed elsewhere herein. In an example, the position calculator 324 may receive pathway information from the subject tracker 320 and determine a position of the robot unit 102 with an appropriate view of the pathway. The position calculator 324 may be coupled to the subject tracker 320 to receive pathway information. The position calculator 324 may be coupled to the gait data processor 326 to provide information on the position of the robot unit 102 and/or sensor(s) 204, which the gait data processor 326 may use to capture sensor data. By way of example, the position calculator 324 may be executed by making a procedure call, calling an object-oriented method, or invoking another suitable process. For instance, a main program of the gait analyzer 208, gait data processor 326, an external or internal API, or another component, may instantiate the position calculator 324, although other execution paths are also applicable and contemplated.

In some implementations, the position calculator 324 may execute a feedback loop that automatically repositions the robot unit 102 as sensor data is captured and/or processed. For example, the gait data processor 326 may capture data reflecting that a portion of the subject 104 (e.g., a head, a foot, etc.) is not in the view of the sensor(s) 204 (e.g., not within the frame). In response to receiving this data, the position calculator 324 may correspondingly send a signal to the actuator(s) 214 to move the sensor(s) 204 and or position of the robot unit 102 to improve the capture of the sensor data for gait analysis.

In some implementations, the position calculator 324 is adapted for cooperation and communication with the processor(s) 302, the memory(ies) 304 and other components of the example computing device 300 via the bus 216. The position calculator 324 may store data and commands received related to the position of the robot unit 102 and/or sensor(s) 204 in the memory(ies) 304 and/or storage device 312. The position calculator 324 may be coupled to output device(s) to output information to a subject 104 and/or other objects in the surroundings. The position calculator 324 may be coupled to input device(s) to receive information from a subject 104 and/or other objects in the surroundings. The position calculator 324 may be coupled to the actuator controller for controlling the actuator(s) 214 in order to control the positions of the sensor(s) 204 and/or position of the robot unit 102 as discussed elsewhere, herein.

The gait data processor 326 includes computer logic operable to collect sensor data and generate gait data. In some implementations, capturing sensor data may include receiving pathway information from the subject tracker 320, position information from the position calculator 324, and an approach from the approach identifier 322 for the gait data processor 326 to use to generate the gait data, as discussed elsewhere herein. In an example, the gait data processor 326 may receive pathway information from the subject tracker 320 that the subject is moving down a hallway and position information from the position calculator 324 that the robot unit 102 is positioned along the wall of the hallway with a view of the pathway. The gait data processor 328 may then use a hybrid approach received from the approach identifier 324 to begin collecting sensor data (e.g., for use as gait data) capturing the subject 104 as the subject 104 moves down the hallway. The gait data processor 326 may be coupled to the subject tracker 320, approach identifier 322, and/or the position calculator 324. By way of example, the gait data processor 326 may be executed by making a procedure call, calling an object-oriented method, or invoking another suitable process. For instance, a main program of the gait analyzer 208, approach identifier 322, an external or internal API, or another component, may instantiate the gait data processor 326, although other execution paths are also applicable and contemplated.

In some implementations, the gait data processor 326 is adapted for cooperation and communication with the processor(s) 302, the memory(ies) 304 and other components of the example computing device 300 via the bus 216. The gait data processor 326 may store data and commands related to gait data collected in the memory(ies) 304 and/or storage device 312. The gait data processor 326 may be coupled to output device(s) to output information to a subject 104 and/or other objects in the surroundings. The gait data processor 326 may be coupled to input device(s) to receive information from a subject 104 and/or other objects in the surroundings.

The guidance provider 328 includes computer logic operable to provide guidance to the subject 104 of where to move along a pathway. In some implementations, providing guidance to the subject 104 may include highlighting a pathway using output device(s), such as projecting a light or laser on the pathway, displaying a route on a screen, emitting audio instructions to the user, etc., as discussed elsewhere herein. In an example, the guidance provider 328 may be coupled to receive pathway information from the subject tracker 320 and position information from the position calculator 324, and may use the pathway information and position information to provide movement guidance during a data collection period. By way of example, the guidance provider 328 may be executed by making a procedure call, calling an object-oriented method, or invoking another suitable process. For instance, a main program of the gait analyzer 208, gait data processor 326, an external or internal API, or another component, may instantiate the guidance provider 328, although other execution paths are also applicable and contemplated.

In some implementations, the guidance provider 328 is adapted for cooperation and communication with the processor(s) 302, the memory(ies) 304 and other components of the example computing device 300 via the bus 216. The guidance provider 328 may store data and commands received related to providing guidance in the memory(ies) 304 and/or storage device 312. The guidance provider 328 may be coupled to output device(s) to output information to a subject 104 and/or other objects in the surroundings. The guidance provider 328 may be coupled to input device(s) to receive information from a subject 104 and/or other objects in the surroundings. The guidance provider 328 may be coupled to the actuator controller for controlling the actuator(s) 214 as discussed elsewhere, herein.

Figure 3B:
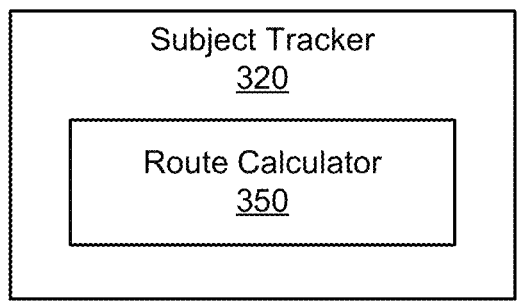
FIG. 3B is a block diagram of an example subject tracker.

FIG. 3B is a block diagram of an example subject tracker 320. The subject tracker 320 may include a route calculator 350. The route calculator 350 may use the data provided by the sensor(s) 204 to determine a potential future route of the subject 104. The potential future route may then be used by the position calculator 324 to determine where the robot unit 102 needs to be positioned to have sensor(s) 204 views of the potential future route. The route calculator 250 may be adapted for cooperation and communication with the processor(s) 302, the memory(ies) 304, and other components of the example computing device 300. The route calculator 350 may be executed in a manner similar to those discussed above with reference to the other components of the gait analyzer 208. The route calculator 350 may be coupled to the storage device 312 and/or memory(ies) 314 to store and retrieve data such as approach data, sensor data, pathway data, etc.

Figure 3C:
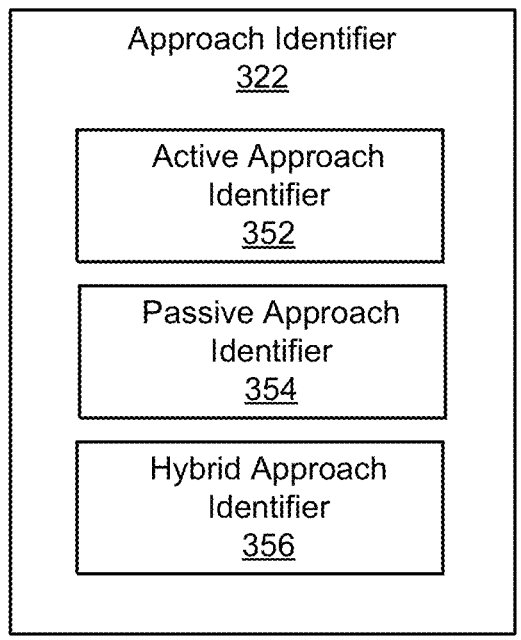
FIG. 3C is a block diagram of an approach identifier.

FIG. 3C is a block diagram of an example approach identifier 322. The approach identifier 322 may include one or more of, an active approach identifier 352, a passive approach identifier 354, and/or a hybrid approach identifier 356. The approach identifiers 352, 354, and/or 356 may be adapted for cooperation and communication with one another, other components of the gait analyzer 208, the processor(s) 302, the memory(ies) 304, and other components of the example computing device 300. The approach identifiers 352, 354, and/or 356 may be executed in a manner similar to those discussed above with reference to the other components of the gait analyzer 208.

The active approach identifier 352 may use the sensor data provided by sensor(s) 204 and/or the pathway information provided by the subject tracker 320 to determine an active approach may be used to collect sensor data. The passive approach identifier 354 may use the sensor data provided by sensor(s) 204 and/or the pathway information provided by the subject tracker 320 to determine a passive approach may be used to collect sensor data. The hybrid approach identifier 356 may use the sensor data provided by sensor(s) 204 and/or the pathway information provided by the subject tracker 320 to determine a hybrid approach may be used to collect sensor data. Each of these components 352, 354, and 356 may be coupled to the storage device 312 and/or memory(ies) 314 to store and retrieve data such as approach data, pathway data, sensor data, gait data, etc. These components are described in further detail below with reference to at least FIGS. 4 and 5A-5D.

Figure 4:
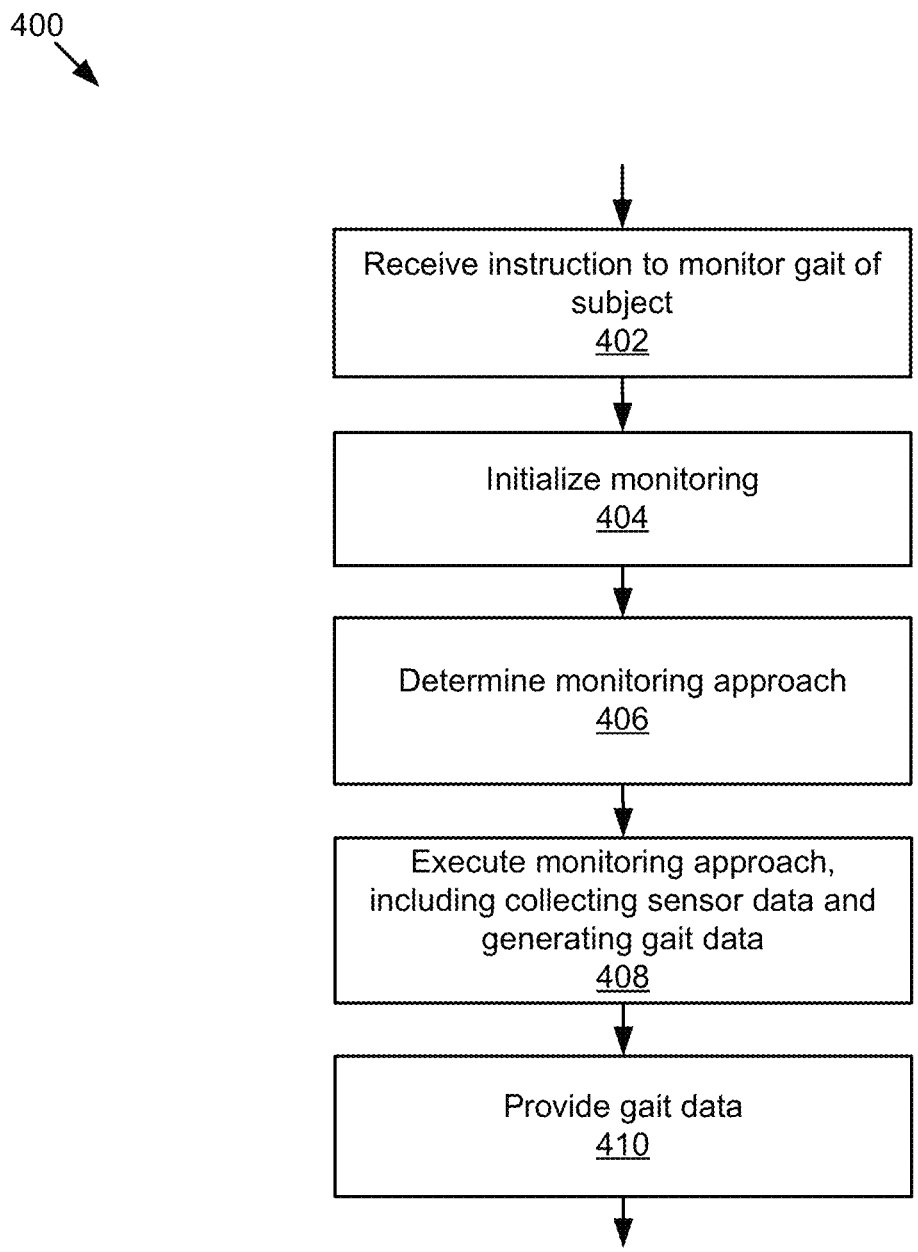
FIG. 4 is a flowchart of an example method for performing gait analysis using a robot unit.

FIG. 4 is a flowchart of an example method 400 for performing gait analysis using a robot unit 102. At block 402, the subject tracker 320 receives an instruction to monitor the gait of the subject 104. The instruction may be autonomously generated and received (e.g., responsive to a triggering event), may be received responsive to input by a stakeholder (e.g., a voice command by the subject 104 or another user), etc. For example, the instruction may be received responsive to input from a physician for the robot unit 102 to capture information related to the subject 104 using the sensor(s) 204. Examples of input may include input captured by a sensor 204 (e.g., an audio signal, a pointer device and/or touchscreen input, a keyboard stroke, input received from a client device 232 via the network 220, etc.). Examples of an autonomous trigger include a timer, certain criteria being met (e.g., walking down a hallway, etc.), etc.

At block 404, responsive to receiving the instruction, the gait data processor 326 initializes monitoring of the subject 104. Initializing monitoring of the subject may include tracking the subject 104 using one or more of the sensor(s) 204. In some implementations, the method 400 instantiates the subject tracker 320 to receive an initial location of the subject 104 and/or instantiates the position calculator 324 to receive an initial position of the robot unit 102. In some implementations, the gait data processor 326 may signal the subject tracker 320 and/or the position calculator 324 to continue to monitor the subject 104 and/or position of the robot unit 102, respectively, for a specific duration, continually, until a stop tracking command is issued, and/or based on other conditions, etc.

By way of example, in some implementations, the position calculator 324 may receive signals from the subject tracker 204, which is monitoring the subject 104 as the subject moves through the environment, instructing the position calculator 324 to generate and send signals to the actuators 214 to move the robot unit 102 in a manner that keeps the subject 104 in view of the sensor(s) 204. For example, the monitoring instruction received by the subject tracker 320 may be instructions for the robot unit 102 to capture images/video of the subject 104 moving around in a home environment over a period of time.

At block 406, the approach identifier 322 determines a monitoring approach for capturing sensor data. In some implementations, the approach identifier 322 receives signals from the gait data processor 326, including the initial location of the subject 104 and the initial position of the robot unit 102, which identify the monitoring approach to be used to monitor the subject 104. In some implementations, the approach identifier 322 may receive location information from the subject tracker 320 related to the location of the subject 104 in the environment, and the approach identifier 322 may use the location data to identify an appropriate monitoring approach. In some implementations, the approach identifier 322 may receive position information from the position calculator 324 related to the position of the robot unit 102 and may use position data to identify an appropriate monitoring approach. In some implementations, a monitoring approach may include operations for determining suitable pathway portions, determining robot positions, capturing and processing sensor data as a subject 104 moves along the pathway portion(s), etc.

In some implementations, the approach identifier 322 selects between a plurality of available monitoring methods based on characteristics of one or more of the surroundings, the subject 104, and position. For instance, the approach identifier 322 may select between different monitoring approaches based on sensor data received from the sensor(s) 204 meeting pre-determined conditions. Example monitoring methods including an active approach that provides explicit guidance to the subject 104 to generate gait data, a passive approach that passively monitors the user and generates gait data when certain conditions are satisfied, and a hybrid approach that generates gait data based on user movement predictions. As a further example, if the approach identifier 322 receives from the subject tracker 320 information that a potential pathway meets the conditions for an active approach, then the approach identifier 322 may provide the information to use the active approach to the gait data processor 326.

At block 408, the gait data processor 326 executes the monitoring approach. Executing the monitoring approach may include collecting sensor data using the sensor(s) 204 and generating gait data based on the sensor data. For example, for a given monitoring approach the gait data processor 326 may execute the operations comprising that approach to collect sensor data using the sensor(s) 204. In some implementations, the sensor data may include images and/or video of the subject 104 as the subject 104 moves along a pathway for a certain distance. Specifically, the sensor data may capture specific information related to the body movement of the subject 104 (e.g., stride, steps, time to move a certain distance, angle of movements at various joints in the subject 104's body, etc.). The operational parameters for positioning the sensor(s) 204 of the robot unit 102 may be embodied in the monitoring approach described in block 406. For example, the gait data processor 326 may use the monitoring approach determined in block 406 to collect sensor data.

Collecting the sensor data may include positioning the robot unit 102 on the one side of a hallway, opposite a determined pathway down the hallway that the subject 104 may move along, and capturing using the sensor(s) 204 the movement of the subject 104 as the subject 104 moves down the hallway. The gait data processor 326 may then identify portions of the sensor data that include data suitable for gait analysis and generate gait data based on those identified portions. In some implementations, the gait data processor 326 may further analyze the gait data using various standard algorithms, and incorporate the output results into the output gait data. For instance, the gait data processor 326 may analyze the gait data by comparing the gait data with data models 314. The data models 314 may include previously captured gait data of the subject 104 and/or models of gait patterns of various individuals. Comparisons may be performed using standard automated comparison algorithms, such as that used by Stone and Skubic, although other suitable algorithms are also applicable.

At block 410, the gait data processor 326 may provide the gait data generated by it to another component. In some implementations, the gait data may be provided for review by transmitting the data over network 220 and provided to the client device 232 or another component connected to the network 220. In some implementations, the gait data may be displayed on a display of the client device 232, on a display of the robot unit 102, or displayed to the subject 104 by another means. In further implementations, the gait data may be provided over the network 220 to a stakeholder (e.g., the subject 104, a medical physician (e.g., a doctor, a nurse, or another caregiver, etc.), a technician, or another suitable individual). In some instances, the data may be reviewed manually by the stakeholder to perform gait analysis.

The gait analyzer 208 may automatically analyze the gait data using various methods. In some implementations, the gait analyzer 208 may line the gait data up side-by-side in a graphical user interface or other defined medium with previously captured gait data captured in comparable pathway environments with comparable positions. In some implementations, the gait data may be compared side-by-side in an augmented reality system, using the comparable positions as the frame of reference. Changes in the data may from a baseline may be illustrated and/or highlighted in an interface accessed by a stakeholder, such as a physician. In further implementations, as part of the gait analysis performed in block 408 or subsequent to the provisioning of the data, a computer algorithm could generate alerts as a result of significant deviations from a baseline, enabling autonomous detection. Other methods for analyzing and displaying gait analysis results are also possible and contemplated.

FIGS. 5A-5E are flowcharts of an example method 500 of determining a monitoring approach. In some implementations, the operations in the method 500 may reflect various operations executable under block 406 of FIG. 4. In FIG.

5A, the approach identifier 322 determines an approach for the gait data processor 326 to collect and process sensor data into gait data. In some implementations, the approach identifier 322 may receive an initial location from the subject tracker 320 and/or an initial position from the position calculator 324. At block 502, the active approach identifier 352 determines whether an active monitoring approach condition has been met. Active monitoring approach conditions may include one or more conditions that are detected and/or determined by the active approach identifier 352 in order for the robot unit 102 to engage in an active monitoring approach to capture gait data.

In some implementations, the active approach identifier 352 may automatically begin determining if the active monitoring approach conditions have been met. In further implementations, the active approach identifier 352 may wait for an external input directing the active approach identifier 352 to determine if active monitoring approach conditions have been met. Active monitoring approach conditions may include autonomously identifying in advance a suitable segment of a pathway, dynamically detecting a segment of the pathway is suitable, receiving information related to a suitable pathway from a stakeholder (e.g., the subject, a technician, the physician, etc.), identifying that the subject 104 may be capable of receiving directions, and identifying a command to use active approach monitoring (e.g., audio command, command input on client device 232, etc.). At block 504, the gait data processor 326 may use the active monitoring approach in response to determining that the active monitoring approach conditions have been met. The active monitoring approach conditions have been met when a threshold amount of the approach conditions have been identified and the threshold may be determined as the minimum amount of approach conditions that may be used to capture sensor data. An example of an active monitoring approach is described with reference to FIG. 5B.

At block 506, the passive approach identifier 354 determines whether a passive monitoring approach condition has been met. Passive monitoring approach conditions may include one or more conditions that are detected and/or determined by the passive approach identifier 354 in order for the robot unit 102 to engage in a passive monitoring approach to capture sensor data. Passive monitoring approach conditions may include identifying conditions in the environment that are suitable for capturing sensor data, including a pathway portion and a position for the robot unit to view the pathway portion. For example, the passive monitoring approach conditions may include identifying a portion of a pathway in the environment that is a suitable distance for the subject 104 to move along in a relatively straight line and a position along the opposite side of the hallway that provides the robot unit 102 with a view of the pathway. In some embodiments, the passive monitoring approach conditions comprise the gait criteria discussed above.

In some implementations, the passive approach identifier 354 may automatically begin determining if the passive monitoring approach conditions have been met. In further implementations, the passive approach identifier 354 may wait for an external input directing the passive approach identifier 354 to determine if passive monitoring approach conditions have been met.

Passive monitoring approach conditions may include analyzing a set of sensor data captured by the sensor(s) 204 at the position and with of the view of the pathway. This analyzed set of sensor data may be compared to gait criteria, as discussed above, to determine if they are suitable for performing gait analysis. In some embodiments, data models 314 embodying various suitable pathway portions may be stored in the storage device 312, and the passive approach identifying 354 may compare the analyzed set of sensor data to the data models 314 to determine a match, and based on the match, may determine the portion of the pathway represented by the set of sensor data to be suitable for gait analysis.

At block 508, the gait data processor 326 may use a passive monitoring approach in response to determining the passive monitoring approach conditions have been met. Passive monitoring approach conditions have been met when a threshold amount of passive monitoring approach conditions have been identified and the threshold may be determined as the minimum amount of approach conditions that may be used to capture sensor data. An example of a passive monitoring approach is described with reference to FIG. 5C.

At block 510, the hybrid approach identifier 356 determines whether a hybrid monitoring approach condition has been met. Hybrid monitoring approach conditions may include one or more conditions that are detected and/or determined by the hybrid approach identifier 356 in order for the robot unit 102 to engage in a hybrid monitoring approach to capture sensor data.

Hybrid monitoring approach conditions may include identifying potential pathways the subject 104 may move along using the route calculator 350, determining if the potential pathways include possible positions for the robot unit 102 and/or the sensor(s) 204 to capture sensor data along the potential pathways, identifying the ability of the robot unit 102 to preposition along the possible positions, and/or calculating the likelihood of the subject 104 to move along a specific potential pathway.

In some implementations, the hybrid approach identifier 356 may automatically begin determining if the hybrid monitoring approach conditions have been met. In further implementations, the hybrid approach identifier 356 may wait for an external input directing the hybrid approach identifier 356 to determine if hybrid monitoring conditions have been met. At block 512, the gait data processor 326 may use a hybrid monitoring approach in response to determining the hybrid monitoring approach conditions have been met. Hybrid monitoring approach conditions are met when a threshold amount of hybrid monitoring approach conditions are identified and the threshold may be determined as the minimum amount of approach conditions that may be used to capture sensor data.

In some implementations, the approach identifier 322 may be preprogrammed to select a specific approach in every instance, whereas in further implementations, the approach identifier 322 may determine if approach conditions are met for one or more of the approaches in order to provide a more adaptable sensor data collection for gait analysis over a wide variety of environments and situations. An example of a hybrid monitoring approach is described with reference to FIG. 5D.

Figure 5A:
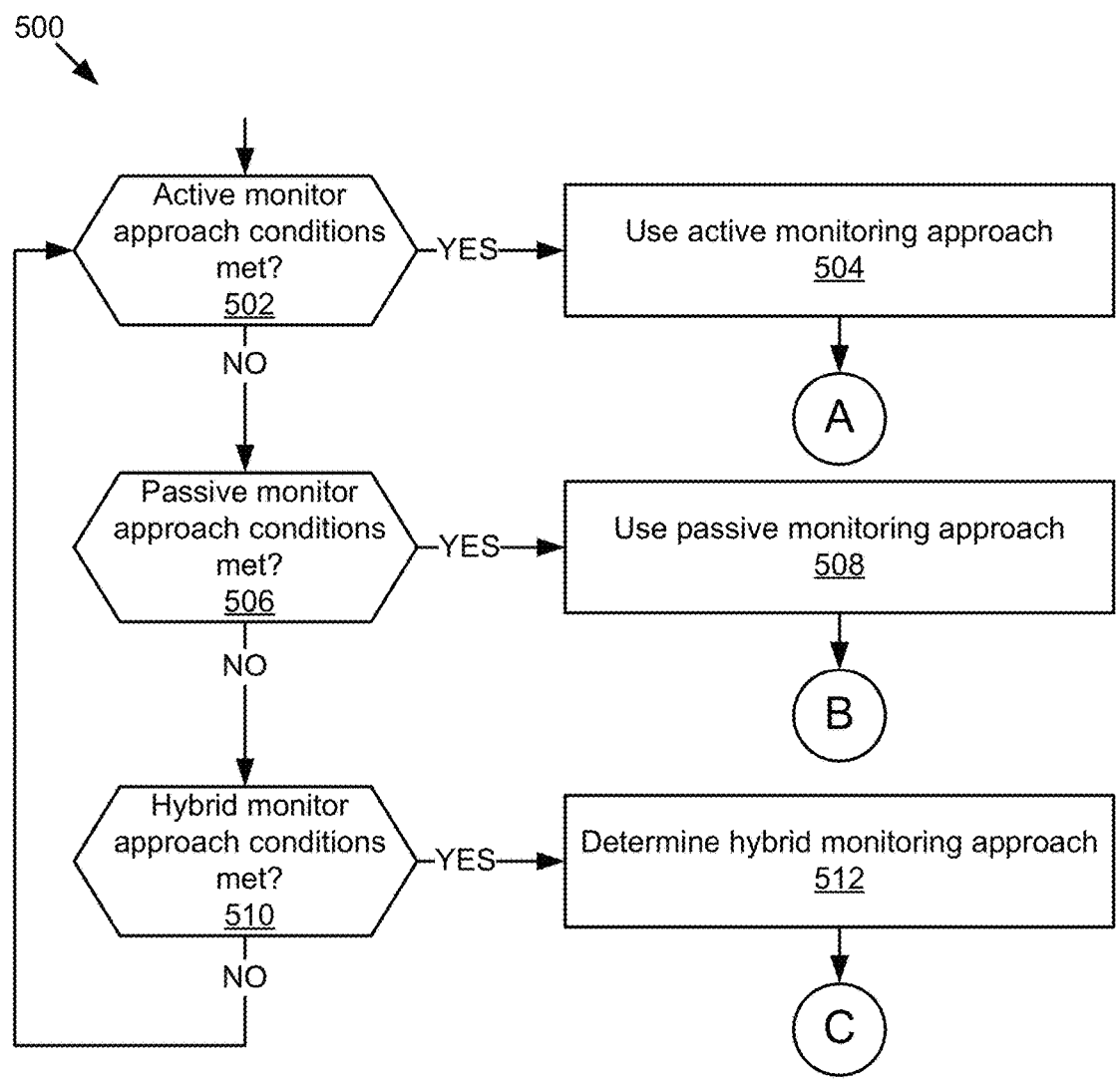
FIGS. 5A-5D are flowcharts of example methods for collecting sensor data for gait analysis.
Figure 5B:
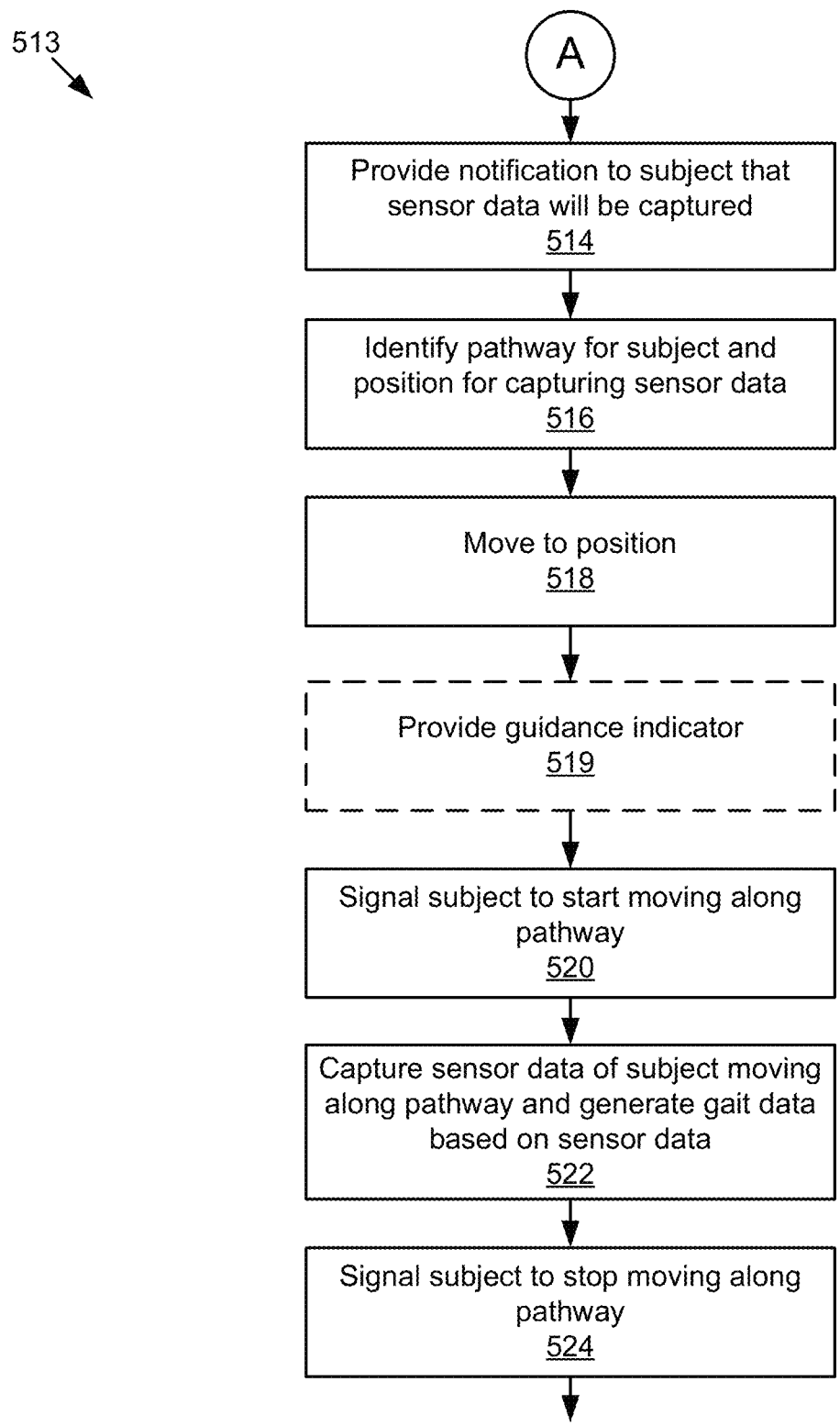

With reference to FIG. 5B, a block-diagram of a method 513 for an active monitoring approach to collect sensor data is depicted. In some implementations, the operations in the method 513 may reflect various operations executable under block 408 of FIG. 4.

At block 514, the guidance provider 328 may provide a notification to the subject 104 that sensor data for gait analysis will be captured. The notification that sensor data for gait analysis will be captured may be provided by output device(s) and may include one or more of, an audible message, a message on a display screen, a tone or other audible noise to signal to the subject 104 that sensor data may be captured, etc. In some implementations, the notification may be provided to the client device 232, such as an on-screen message, an audible alert through an output device on the client device 232, etc. In further implementations, the notification may be provided to the subjects 104 to position themselves along a pre-designated pathway. For example, the guidance provider 328 may be pre-programmed using the active monitoring approach to provide using output device(s) the message, "It's time for your gait test," signaling to the subject 104 that gait monitoring will soon begin, although it should be understood that numerous other variations and alternatives are also possible.

In some implementations, the gait data processor 326 may execute a procedure call to a method with parameters for executing collecting sensor data using an active monitoring approach. The method may be stored in memory(ies) 304 and accessible by the gait data processor 326 and/or other components of the computing device 300 for execution. In further implementations, the gait data processor 326 may receive data describing the various operations for the active monitoring approach (e.g., as embodied by a data model 314) from the approach identifier 322 and/or the storage device 312, and the gait data processor 326 may perform the operations.

At block 516, the subject tracker 320 identifies a pathway for the subject 104 to move along and a position for capturing the sensor data. In some implementations, the gait data processor 326 may receive an autonomously identified pathway from the route calculator 350. The route calculator 350 may use standard image processing techniques to identify pathways in the data captured by the sensor(s) 204. The route calculator 350 may identify pathways by identifying portions of the environment that the subject 104 could move a certain distance (e.g., 10 feet in one example, or any distance that could be used for gait analysis) in a straight line. In further implementations, the subject tracker 320 may identify a portion of a pre-defined pathway (all, part, etc.). The pre-defined pathway may be a portion of the environment that allows the subject 104 to walk in a straight line as determined manually by the subject 104, a physician, a technician, etc.

The gait data processor 326 may receive from the position calculator 324 a position of where a sensor(s) 204 may be located to capture the subject 104 moving along the pathway. The position may include a clear view of the pathway based on the capabilities of the sensor(s) 204. For example, the pathway may a portion of a hallway and the position may be a spot along the opposite side of the hallway relative to the pathway where a camera may be able to capture video data of the subject 104 moving along the pathway. In some implementations, the sensor(s) 204 may be able to view the pathway from the position without moving or altering the sensor(s) 204. In further implementations, multiple positions and/or angles may be identified and the sensor(s) 204 may move to multiple positions and/or angles to view the subject 104 moving along the pathway.

At block 518, the position calculator 324 may move the sensor(s) to the identified position. In some implementations, the position calculator 324 may be adapted to provide commands in the form of signals to the actuator(s) 114 of the robot unit 102 to move the robot unit 102 to the position. For example, the position calculator 324 may provide a command to the actuator(s) 214 to move the robot unit 102 to the middle of the hallway and position sensor(s) 204 to view the opposite side of the hallway.

At block 519, in some implementations, the guidance provider 328 may provide a guidance indicator. The guidance indicator may be an indicator to the subject 104 of where along the pathway the subject 104 needs to move for sensor data to be captured. For example, the guidance indicator may be lines on the floor via a laser, signals through a vibration belt, lights and/or sounds indicating proper movement, etc.

At block 520, the guidance provider 328 signals the subject 104 to start moving along the pathway. The signal to start may be provided by output device(s) and may include one or more of, an audible message, a message on a display screen, a tone or other audible noise to signal to the subject 104 that sensor data may be captured, etc. For example, the guidance provider 328 may be pre-programmed using the active monitoring approach to provide using output device(s) the message, "Please walk ten feet forward," signaling to the subject 104 to begin moving along the pathway.

At block 522, the gait data processor 326 captures sensor data of the subject 104 moving along the pathway and generates gait data based on the sensor data. The sensor data may be captured by the sensor(s) 204 and may include one or more of images, video, audio, depth images, etc. of the subject 104 moving along the pathway. In some implementations, the gait data processor 326 may be configured to capture sensor data once the subject 104 has begun moving at a habitual speed. For example, the guidance provider 328 may have the subject 104 begin moving along the pathway for an initial period (e.g., a time period, a distance such as 2 meters, etc.) before the gait data processor 326 captures sensor data.

In some implementations, the gait data processor 326 may complete capturing of the sensor data before instructing the guidance provider 328 to inform the subject 104 that collection of sensor data for gait analysis is complete (e.g., allow subject 104 to move through the end of the pathway before slowing down) as described with reference to block 524.

The gait data processor 326 may be configured capture information about the positions and angles of the sensor(s) 204 and the distances between the sensor(s) 204 and the subject 104 as the subject 104 moves along the pathway, for additional analysis, such as accounting for motion anomalies, etc. The gait data processor 326 may be configured to capture various types of sensor data, for example, the gait data processor 326 may capture sensor data of the subject 104 as the subject 104 moves in different ways (e.g., walking, jogging, running, skipping, jumping, etc.). In some cases, the gait data processor 326 may be able to capture sensor data of various clinical trials, such as the habitual gait speed (HGS), comfortable gait speed (CGS), fast gait speed (FGS), and/or timed-up and go (TUG). The gait data processor 326 may then generate gait data based on the sensor data. For instance, the gait data may be generated by determining portions of the sensor data where the passive monitoring approach conditions were met, although gait data and/or sensor data may be incorporated.

At block 524, the guidance provider 328 informs the subject 104 to stop moving along the pathway responsive to completion of the data collection. Completion of the data collection may be determined by the subject tracker 320 signaling that the subject 104 has reached the end point of the pathway portion, the subject 104 has deviated from the pathway portion beyond an allowable threshold, etc. Further, completion of the data collection may be determined by the gait data processor 326 determining that sufficient sensor data has been processed for a given pathway portion, or may be determined by input from a stakeholder via an input device that collection should cease. Other variations for determining completion are also possible and contemplated.

The signal to the subject 104 to stop moving may be provided by output device(s) and may include one or more of, an audible message, a message on a display screen, a tone or other audible noise to signal to the subject 104 that sensor data may be captured, etc. For example, the guidance provider 328 may be pre-programmed using the active monitoring approach to provide using output device(s) the message, "Gait analysis complete," signaling to the subject 104 to that sensor data is no longer being captured by the sensor(s) 204, although it should be understood that numerous other alternatives and variations are also possible and contemplated.

Figure 5C:
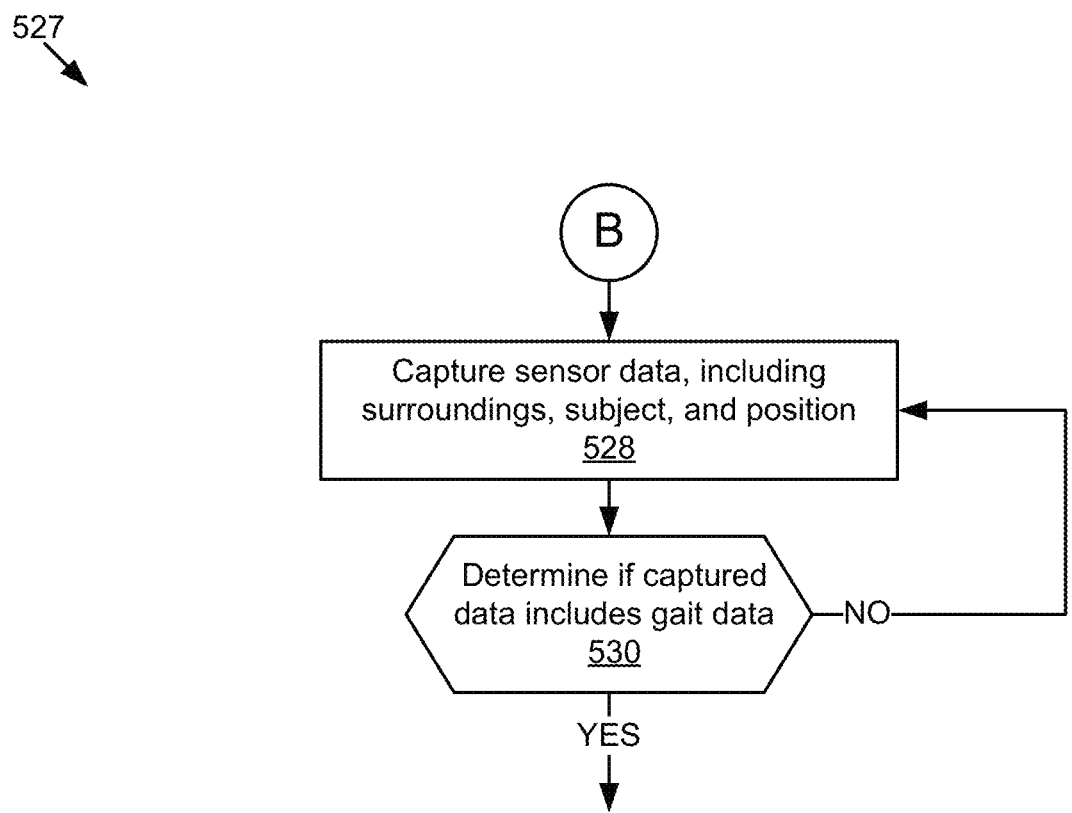

With reference to FIG. 5C, a block-diagram of a method 527 of using a passive monitoring approach to collect sensor data is depicted. In some implementations, the operations in the method 527 may reflect various operations executable under block 408 of FIG. 4.

At block 528, the gait data processor 326 may capture sensor data for gait analysis using the sensor(s) 204. In some implementations, the gait data processor 326 may execute a procedure call to a method with parameters for executing collecting sensor data using a passive monitoring approach. The method may be stored in memory(ies) 304 and accessible by the gait data processor 326 and/or other components of the computing device 300 for execution. In further implementations, the gait data processor 326 may receive data describing the various operations for the passive monitoring approach (e.g., as embodied by a data model 314) from the approach identifier 322 and/or the storage device 312, and the gait data processor 326 may perform the operations.

In some implementations, the gait data processor 326 may continuously capture sensor data using the sensor(s) 204 as part of the process of monitoring the subject 104. To position the sensor(s) 204, the position calculator 324 determines the position of the subject based on tracking signals received from the subject tracker 320. The subject tracker 320 may use standard image recognition and/or processing techniques to identify pathways that the subject 104 has moved along based on the sensor data being received from the sensor(s) 204.

At block 530, the gait data processor 326 may determine if the captured sensor data includes gait data. To make this determination, the gait data processor 326 determines that the sensor data for the identified position(s) and pathway portion satisfies the gait criteria, as discussed above. In some implementations, if the gait data processor 326 determines that sensor data does not include gait data (data suitable for gait analysis), then the gait data processor 326 may continue to capture sensor data, as discussed with reference to block 528.

Figure 5D:
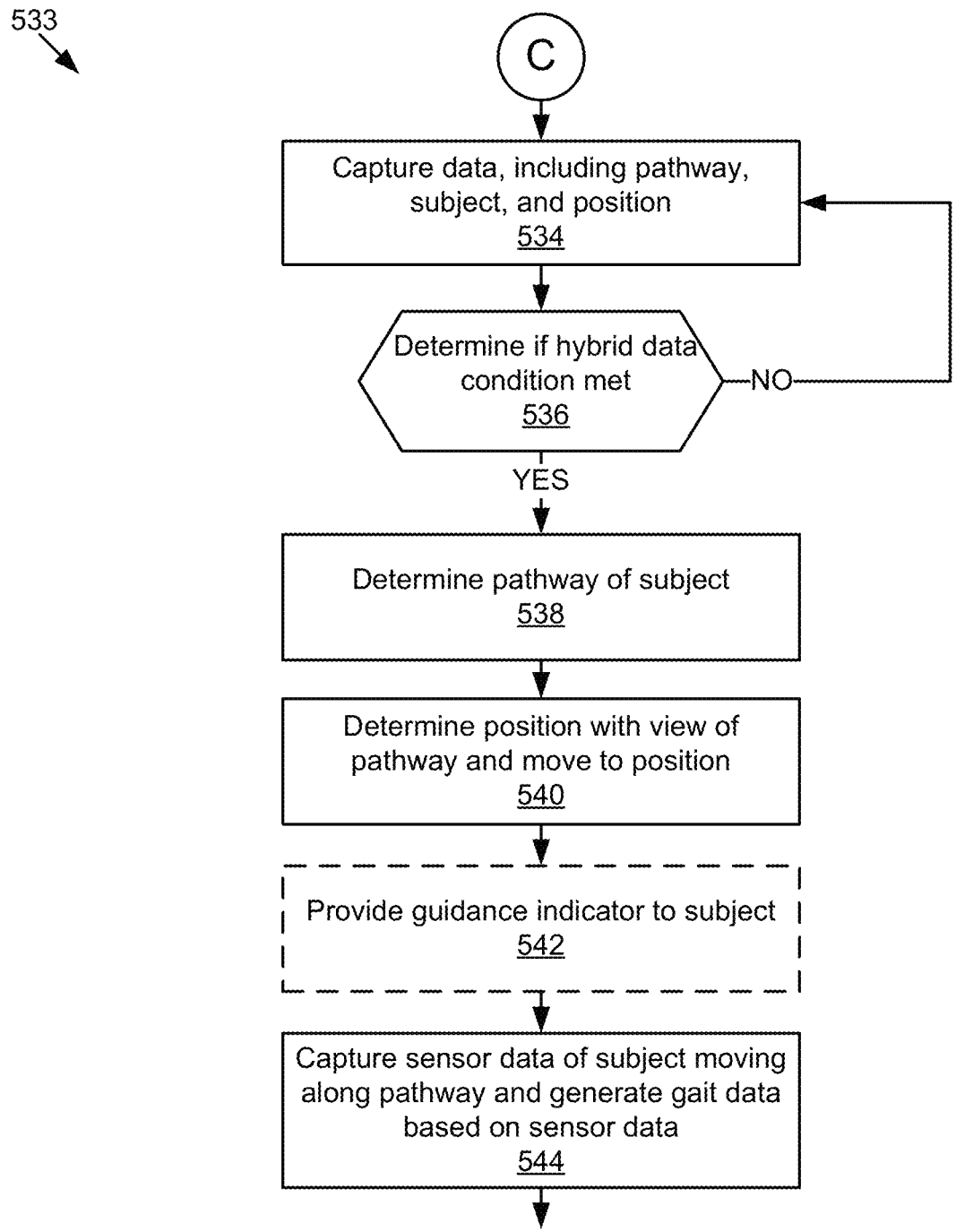

With reference to FIG. 5D, a block-diagram of a method 533 of using a hybrid monitoring approach to collect sensor data for gait analysis is depicted. In some implementations, the operations in the method 533 may reflect various operations executable under block 408 of FIG. 4.

In some implementations, the gait data processor 326 may execute a procedure call to a method with parameters for executing collecting sensor data using a hybrid monitoring approach. The method may be stored in memory(ies) 304 and accessible by the gait data processor 326 and/or other components of the computing device 300 for execution. In further implementations, the gait data processor 326 may receive data describing the various operations for the hybrid monitoring approach (e.g., as embodied by a data model 314) from the approach identifier 322 and/or the storage device 312, and the gait data processor 326 may perform the operations.

At block 534, the gait data processor 326 may capture sensor data using the sensor(s) 204. In some implementations, the gait data processor 326 may continuously capture sensor data using the sensor(s) 204 as part of the process of monitoring the subject 104.

At block 536, the gait data processor 326 may determine if hybrid data conditions have been met. Hybrid data conditions may include, identifying a potential pathway in the surroundings that the subject 104 is likely to move along, identifying a position of sensor(s) 204 with a view of a portion of the potential pathway, and determining that performing the hybrid monitoring approach to collect sensor data will allow the subject tracker 320 to continue monitoring the subject 104.

For example, the route calculator 350 may identify that the portion of the potential pathway is a hallway that the subject 104 is likely to move along and the approach identifier 322 may identify that a position opposite the portion of the potential pathway includes a view of the portion of the potential pathway. The determinations made by the route calculator 350 and the approach identifier 322 may be provided as data to the gait data processor 326 for processing. In some cases, if the position calculator 324 directs the sensor(s) to move to the position, then the subject tracker 320 will not be able to monitor the subject 104 since a wall will block the subject 104 from a view of the sensor(s) 204. Therefore, the gait data processor 326 may determine that the hybrid data conditions have not been met and continue to capture sensor data using the sensor(s) 204.

At block 538, in response to determining that the hybrid data conditions have been met based on a corresponding signal received from the gait data processor 326, the route calculator 350 determines a likely pathway of the subject 104. In some implementations, the route calculator 350 may determine the likely pathway including where the subject 104 is going by using route prediction. The route calculator 350 may receive data from the sensor(s) 204 and/or the gait data processor 326 including, the direction the subject 104 is moving, the direction the subject 104 is facing, audio of the subject 104, previous history of subject 104's movements, patterns of movement of various subjects over time, etc. and the route calculator 350 may use the sensor data to predict likely pathways the subject 104 may move along in a future period of time.

The gait data processor 326 may receive the likely pathway from the route calculator 350 and determine if the likely pathway is a potential pathway determined above with respect to the hybrid data conditions, as discussed elsewhere herein. If the gait data processor 326 determines that the likely path is a potential path for hybrid data conditions, then the gait data processor 326 may determine that the pathway is a pathway for collecting sensor data using hybrid data conditions. For example, the route calculator 350 may use the sensor data indicating that the subject 104 is heading through a lobby towards the hallway and using the historical data of the subject 104 moving through the lobby towards the lobby, identify the hallway as a likely pathway for capturing sensor data in the future.

At block 540, the position calculator 324 determines a position with a view of the pathway based on data describing the likely pathway received from the subject tracker 320, and may send signals to the actuator(s) 214 to move to the position. The position may be a potential position identified by the position calculator 324, as discussed elsewhere herein.

The position calculator 324 may send signals to the actuator(s) 214 to move the sensor(s) 204 and/or the robot unit 102 to the position, as discussed elsewhere herein. For example, the position calculator 324 may send a signal to the actuator(s) to navigate the robot unit 102 to the opposite wall of the hallway along which the subject 104 is likely to move down.

At block 542, the guidance provider 328 may provide a guidance indicator to the subject 104 as the subject 104 moves to the pathway. The guidance indicator may signal to the subject 104 where to move along the pathway for the sensor(s) 204 to capture sensor data. The guidance indicator may be similar to the guidance indicator described in the active monitoring approach, discussed elsewhere herein. The guidance provider 328 may receive tracking signals from the subject tracker 320, which is tracking movement of the subject 104, and may base guidance on the position and movement of the subject 104. This is advantageous, particularly if corrective guidance is needed to keep the subject 104 on course.

At block 544, the gait data processor 326 captures sensor data of the subject 104 moving along the pathway. In some implementations, the gait data processor 326 may be configured to capture sensor data once the subject 104 has begun moving at a habitual speed. For example, the gait data processor 326 may wait for the subject 104 to begin moving along the pathway for an initial period (e.g., a time period, a distance such as 2 meters, etc.) before the gait data processor 326 captures sensor data.

The gait data processor 326 may be configured capture information about the positions and angles of the sensor(s) 204 and the distances between the sensor(s) 204 and the subject 104 as the subject 104 moves along the pathway, for additional analysis, such as accounting for motion anomalies, etc. The gait data processor 326 may be configured to capture various types of sensor data, for example, the gait data processor 326 may capture sensor data of the subject 104 as the subject 104 moves in different ways (e.g., walking, jogging, running, skipping, jumping, etc.). In further implementations, the gait data processor 326 may be able to capture sensor data of various clinical trials, such as the habitual gait speed (HGS), comfortable gait speed (CGS), fast gait speed (FGS), and/or timed-up and go (TUG). The gait data processor 326 may generate gait data using the sensor data. For example, the gait data may be generated by identifying portions of the sensor data that meet the hybrid monitoring approach conditions and generating the gait data based on those identified portions, although it should be understood that other sensor and/or gait data may be incorporated.

At block 546, the gait data processor 326 provides the gait data to one or more of the gait analyzer 208, subject 104, doctor, and/or technician, etc. for gait analysis as discussed elsewhere herein. For example, the gait data may include video data of the subject 104 moving down the hallway and the video data may be provided to a doctor. In some implementations, the gait data processor 326 may provide a copy of the captured data that includes the gait data. In further implementations, the gait data processor 326 may provide indicators or timestamps to the portion of the captured data that includes the gait data. In some implementations, the gait data may be provided at different instances, such as immediately after the gait data has been captured and/or identified, at regular intervals, when a significant deviation has been detected and an alert has been generated, etc. as discussed elsewhere herein.

Figure 6:
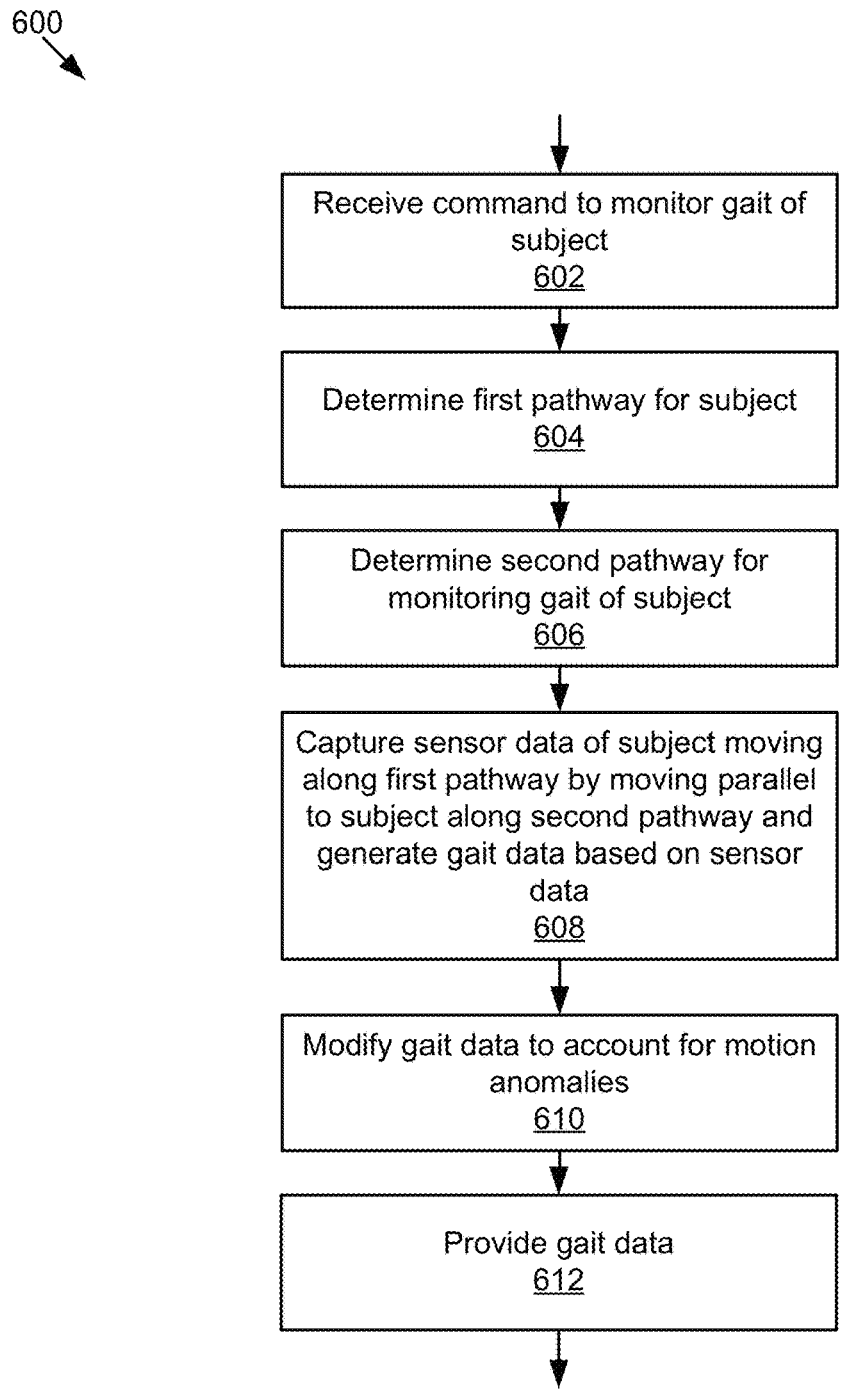
FIG. 6 is a flowchart of a further example method collecting sensor data for gait analysis using a robot unit.

FIG. 6 is a flowchart of another example method 600 for collecting sensor data for gait analysis using a robot unit 102. At block 602, the subject tracker 320 receives an instruction to monitor a gait of the subject 104. The instruction to monitor the gait may include an instruction for the robot unit 102 to begin the process of capturing sensor data for gait analysis as discussed elsewhere herein.

At block 604, the route calculator 350 may determine a first pathway (e.g., including pathway portion(s)) for the subject 104. The first pathway may be or include a pathway portion in the environment of a specific distance (e.g., ten feet, ten meters, etc.) that a subject 104 may move along in a straight line. The first pathway may be similar to other pathways discussed elsewhere herein for the subject 104 to move along while gait data is collected.

At block 606, the route calculator 350 may determine a second pathway for monitoring the gait of the subject 104. The second pathway may be a pathway for robot unit 102 to move along parallel to the first pathway, such that the robot unit 102 may move along the second pathway parallel to the subject 104 as the subject 104 moves along the first pathway to capture sensor data. The route calculator 350 may determine the second pathway using image recognition and/or standard image processing on data of the surroundings collected by the sensor(s) 204. In some implementations, the route calculator 350 may use conditions to determine the second pathway, such as, the second pathway may be unobstructed for the robot unit 102 to navigate along, the second pathway may provide a clear/unobstructed view of the subject 104 as the subject 104 moves along the first pathway, and/or the second pathway may move in a straight line at a specific distance (e.g., a predetermined distance based on the capabilities of the sensor(s) 204) from the first pathway, etc.

At block 608, the gait data processor 326 may capture sensor data of the subject 104 moving along the first pathway by moving the sensor(s) 204 (e.g., of the robot unit 102) parallel to the subject 104 along the second pathway. In some implementations, the position calculator 324 may send commands in the form of signals to the actuator(s) 214 of the robot unit 102 to move along the second pathway and the subject tracker 320 may use data received from the sensor(s) to determine the location of the subject 104 in order to maintain a parallel movement along the second pathway relative to the movement of the subject 104 along the first pathway. For example, the subject 104 may begin moving along one side of a hallway and the robot unit 102 may be positioned on the opposite side of the hallway. As the subject 104 moves, the robot unit 102 moves down the second pathway at a similar speed in order to capture a continuous side view of the subject 104 as they subject 104 moves down the first pathway. This implementation provides sensor data for gait analysis with a consistent perspective of the subject 104, rather than angled sensor data as the subject 104 moves along a pathway relative to a stationary position of sensor(s) 204. The gait data processor 326 may generate gait data based on the sensor data. The gait data may be generated by identifying portions of the sensor data that meet conditions for collecting and/or generating gait data as discussed elsewhere herein.

At block 610, the gait data processor 326 modify the gait data to account for motion anomalies. The motion anomalies may be deviations from the parallel view that the robot unit 102 may encounter as the robot unit 102 navigates the second pathway. For example, the second pathway may be slightly uneven, causing a camera sensor to have a tilted view of the subject 104 as the robot unit 102 navigates the slightly uneven section. The gait data processor 326 may use sensor data captured by the sensor(s) 204, which include the deviations from the standard sensor positions, and may use standard image correction techniques to modify the gait data to account for motion anomalies introduced by the deviations. At block 612, the gait data processor 326 may provide the gait data as discussed elsewhere herein.

It should be understood that the methods 400, 500, 513, 527, 533, and 600 are provided by way of example, and that variations and combinations of these methods, as well as other methods, are contemplated. For example, in some embodiments, at least a portion of one or more of the methods 500, 513, 527, and 533 represent various segments of one or more larger methods (e.g., method 400) and may be concatenated or various steps of these methods may be combined to produce other methods which are encompassed by the present disclosure. Additionally, it should be understood that various operations in the methods 400, 500, 513, 527, 533, and 600 are iterative, and thus repeated as many times as necessary generate the results described herein. Further the ordering of the operations in the methods 400, 500, 513, 527, 533, and 600 is provided by way of example and it should be understood that various operations may occur earlier and/or later in the method without departing from the scope thereof.

In the above description, for purposes of explanation, numerous specific details are set forth in order to provide a thorough understanding of the present disclosure. However, it should be understood that the technology described herein could be practiced without these specific details. Further, various systems, devices, and structures are shown in block diagram form in order to avoid obscuring the description. For instance, various implementations are described as having particular hardware, software, and user interfaces. However, the present disclosure applies to any type of computing device that can receive data and commands, and to any peripheral devices providing services.

In some instances, various implementations may be presented herein in terms of algorithms and symbolic representations of operations on data bits within a computer memory. An algorithm is here, and generally, conceived to be a self-consistent set of operations leading to a desired result. The operations are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the following discussion, it is appreciated that throughout this disclosure, discussions utilizing terms including "processing," "computing," "calculating," "determining," "displaying," or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

Various implementations described herein may relate to an apparatus for performing the operations herein. This apparatus may be specially constructed for the required purposes, or it may comprise a general-purpose computer selectively activated or reconfigured by a computer program stored in the computer. Such a computer program may be stored in a computer readable storage medium, including, but is not limited to, any type of disk including floppy disks, optical disks, CD ROMs, and magnetic disks, read-only memories (ROMs), random access memories (RAMs), EPROMs, EEPROMs, magnetic or optical cards, flash memories including USB keys with non-volatile memory or any type of media suitable for storing electronic instructions, each coupled to a computer system bus.

The technology described herein can take the form of an entirely hardware implementation, an entirely software implementation, or implementations containing both hardware and software elements. For instance, the technology may be implemented in software, which includes but is not limited to firmware, resident software, microcode, etc. Furthermore, the technology can take the form of a computer program product accessible from a computer-usable or computer-readable medium providing program code for use by or in connection with a computer or any instruction execution system. For the purposes of this description, a computer-usable or computer readable medium can be any non-transitory storage apparatus that can contain, store, communicate, propagate, or transport the program for use by or in connection with the instruction execution system, apparatus, or device.

A data processing system suitable for storing and/or executing program code may include at least one processor coupled directly or indirectly to memory elements through a system bus. The memory elements can include local memory employed during actual execution of the program code, bulk storage, and cache memories that provide temporary storage of at least some program code in order to reduce the number of times code must be retrieved from bulk storage during execution. Input/output or I/O devices (including but not limited to keyboards, displays, pointing devices, microphones, speakers, etc.) can be coupled to the system either directly or through intervening I/O controllers.

Network adapters may also be coupled to the system to enable the data processing system to become coupled to other data processing systems, storage devices, remote printers, etc., through intervening private and/or public networks. Wireless (e.g., Wi-Fi™) transceivers, Ethernet adapters, and modems, are just a few examples of network adapters. The private and public networks may have any number of configurations and/or topologies. Data may be transmitted between these devices via the networks using a variety of different communication protocols including, for example, various Internet layer, transport layer, or application layer protocols. For example, data may be transmitted via the networks using transmission control protocol/Internet protocol (TCP/IP), user datagram protocol (UDP), transmission control protocol (TCP), hypertext transfer protocol (HTTP), secure hypertext transfer protocol (HTTPS), dynamic adaptive streaming over HTTP (DASH), real-time streaming protocol (RTSP), real-time transport protocol (RTP) and the real-time transport control protocol (RTCP), voice over Internet protocol (VOIP), file transfer protocol (FTP), Web-Socket (WS), wireless access protocol (WAP), various messaging protocols (SMS, MMS, XMS, IMAP, SMTP, POP, WebDAV, etc.), or other known protocols.

Finally, the structure, algorithms, and/or interfaces presented herein are not inherently related to any particular computer or other apparatus. Various general-purpose systems may be used with programs in accordance with the teachings herein, or it may prove convenient to construct more specialized apparatus to perform the required method blocks. The required structure for a variety of these systems will appear from the description above. In addition, the specification is not described with reference to any particular programming language. It will be appreciated that a variety of programming languages may be used to implement the teachings of the specification as described herein.

The foregoing description has been presented for the purposes of illustration and description. It is not intended to be exhaustive or to limit the specification to the precise form disclosed. Many modifications and variations are possible in light of the above teaching. It is intended that the scope of the disclosure be limited not by this detailed description, but rather by the claims of this application. As will be understood by those familiar with the art, the specification may be embodied in other specific forms without departing from the spirit or essential characteristics thereof. Likewise, the particular naming and division of the modules, routines, features, attributes, methodologies and other aspects are not mandatory or significant, and the mechanisms that implement the specification or its features may have different names, divisions and/or formats.

Furthermore, the modules, routines, features, attributes, methodologies and other aspects of the disclosure can be implemented as software, hardware, firmware, or any combination of the foregoing. Also, wherever a component, an example of which is a module, of the specification is implemented as software, the component can be implemented as a standalone program, as part of a larger program, as a plurality of separate programs, as a statically or dynamically linked library, as a kernel loadable module, as a device driver, and/or in every and any other way known now or in the future. Additionally, the disclosure is in no way limited to implementation in any specific programming language, or for any specific operating system or environment.

What is claimed is:

1. A computer-implemented method comprising:
   receiving, using one or more computer processors, an instruction for a robot unit to monitor a gait of a subject;
   determining, using the one or more computer processors, a potential pathway that the subject is to move along;
   determining, using the one or more computer processors, a pathway portion of the potential pathway, the pathway portion satisfying a gait criteria;
   determining, using the one or more computer processors, a position from which one or more sensors of the robot unit can view the pathway portion that satisfies the gait criteria;
   actuating one or more actuators of the robot unit to move the robot unit to the position;
   capturing, using the one or more sensors of the robot unit, sensor data, the sensor data capturing the subject moving along the pathway portion; and
   generating, using the one or more computer processors, gait data using the sensor data.

2. The method of claim 1, wherein the gait criteria includes one of a pathway portion length parameter, a pathway portion straightness tolerance, and a clearance from obstructions.

3. The method of claim 1, further comprising:
   providing, using an output device, a first guidance indicator to the subject;
   determining, using the one or more computer processors, that the subject has moved to a pre-determined point along the pathway portion; and
   providing, using the output device, a second guidance indicator to the subject.

4. The method of claim 3, wherein the first guidance indicator and the second guidance indicator each include one of an audio message, a laser directed along the pathway portion, and a light highlighting the pathway portion.

5. A computer-implemented method comprising:
   receiving, using one or more computer processors, an instruction to monitor a gait of a subject;
   initializing, using the one or more computer processors, a monitoring approach in response to receiving the instruction to monitor the gait of the subject;
   determining, using the one or more computer processors, a potential pathway that the subject is to move along;
   determining, using the one or more computer processors, a pathway portion of the potential pathway, the pathway portion satisfying a gait criteria;
   moving one or more sensors coupled to the one or more computer processors to a sensor position that has a view of the pathway portion responsive to determining that the pathway portion satisfies the gait criteria;
   collecting, based on the monitoring approach and using the one or more sensors coupled to the one or more computer processors, sensor data capturing movement of the subject along the pathway portion; and
   generating gait data for gait analysis based on the sensor data.

6. The method of claim 5, wherein the monitoring approach is an active monitoring approach and collecting the sensor data includes collecting the sensor data using the active monitoring approach by:
   providing, using an output device coupled to the one or more computer processors, a notification to the subject that the sensor data for gait analysis will be captured;
   providing, using the one or more computer processors, a first guidance to the subject to begin moving along the pathway portion; and
   responsive to the subject beginning to move along the pathway portion, capturing, using the one or more sensors, the sensor data.

7. The method of claim 5, wherein the monitoring approach is a passive monitoring approach, the sensor data includes surroundings data, subject data, and position data, and collecting the sensor data includes collecting the sensor data using the passive monitoring approach by:
   capturing, using the one or more sensors, the sensor data;
   determining, using the one or more computer processors, that the surroundings data, subject data, and position data included in the sensor data meet passive monitoring approach conditions; and
   generating the gait data using the sensor data responsive to the passive monitoring approach conditions being met.

8. The method of claim 7, wherein the passive monitoring conditions include a pre-determined length of a pathway, a stable position for viewing the pathway, and image data of the subject moving along the pathway.

9. The method of claim 5, wherein the monitoring approach is a hybrid monitoring approach and collecting the sensor data includes collecting the sensor data using the hybrid monitoring approach by:

capturing, using the one or more sensors, first sensor data including surroundings data, subject data, and position data;

determining, using the one or more computer processors, that hybrid monitoring conditions have been met based on the first sensor data;

determining, using the one or more computer processors, the pathway portion of the potential pathway based on the first sensor data;

determining, using the one or more computer processors, a position of a housing of the one or more computer processors that provides the one or more sensors coupled to the one or more computer processors with the view of the pathway portion;

actuating one or more actuators coupled to the one or more computer processors to move the housing of the one or more computer processors to the position; and capturing, using the one or more sensors, second sensor data, the second sensor data capturing the subject moving along the pathway portion.

10. The method of claim 9, wherein determining that the hybrid monitoring conditions have been met further comprises:

determining, using the one or more computer processors, that the pathway portion of the potential pathway exceeds a pre-defined length based on the first sensor data; and predicting, using the one or more computer processors, that the subject will move along the pathway portion of the potential pathway within a period based on the first sensor data.

11. The method of claim 5, wherein collecting the sensor data further comprises:

determining, using the one or more computer processors a second pathway parallel to the potential pathway for monitoring the gait of the subject; and capturing, using the one or more sensors, the sensor data by moving a housing of the one or more computer processors along the second pathway parallel to the subject as the subject moves along the potential pathway.

12. The method of claim 5, further comprising:

modifying, using the one or more computer processors, the sensor data to account for motion anomalies.

13. A system comprising:

one or more processors; and one or more memories storing instructions that when executed by the one or more processors, cause the system to perform operations including:

receiving an instruction to monitor a gait of a subject;

initializing a monitoring approach in response to receiving the instruction to monitor the gait of the subject;

determining a potential pathway that the subject is to move along;

determining a pathway portion of the potential pathway, the pathway portion satisfying a gait criteria;

moving one or more sensors coupled to the one or more processors to a sensor position that has a view of the pathway portion responsive to determining that the pathway portion satisfies the gait criteria;

collecting, based on the monitoring approach and using the one or more sensors, sensor data capturing movement of the subject along the pathway portion; and generating gait data for gait analysis based on the sensor data.

14. The system of claim 13, wherein the monitoring approach is an active monitoring approach and collecting the sensor data includes collecting the sensor data using the active monitoring approach by:

providing a notification to the subject that the sensor data for gait analysis will be captured;

providing a first guidance to the subject to begin moving along the pathway portion; and responsive to the subject beginning to move along the pathway portion, capturing the sensor data.

15. The system of claim 13, wherein the monitoring approach is a passive monitoring approach, the sensor data includes surroundings data, subject data, and position data, and collecting the sensor data includes collecting the sensor data using the passive monitoring by:

capturing the sensor data;

determining that the surroundings data, subject data, and position data included in the sensor data meet passive monitoring conditions; and generating the gait data using the sensor data responsive to the passive monitoring approach conditions being met.

16. The system of claim 15, wherein the passive monitoring approach conditions include a pre-determined length of a pathway, a stable position for viewing the pathway, and image data of the subject moving along the pathway.

17. The system of claim 13, wherein the monitoring approach is a hybrid monitoring approach and collecting the sensor data includes collecting the sensor data using the hybrid monitoring approach by:

capturing first sensor data including surroundings data, subject data, and position data;

determining that hybrid monitoring conditions have been met based on the first sensor data;

determining the pathway portion of the potential pathway based on the first sensor data;

determining a position for a housing of the one or more processors that provides the one or more sensors with the view of the pathway portion;

actuating one or more actuators coupled to the one or more processors to move the housing of the one or more processors to the position; and capturing second sensor data, the second sensor data capturing the subject moving along the pathway portion.

18. The system of claim 17, wherein determining that the hybrid monitoring conditions have been met further includes:

determining that the gait criteria of the pathway portion of the potential pathway exceeds a pre-defined length based on the first sensor data; and determining that the subject will move along the pathway portion of the potential pathway within a period based on the first sensor data.

19. The system of claim 13, wherein collecting the sensor data further includes:

determining a second pathway parallel to the potential pathway for monitoring the gait of the subject; and capturing the sensor data by moving a housing of the one or more processors along the second pathway parallel to the subject as the subject moves along the potential pathway.

20. The system of claim 13, wherein collecting the sensor data further includes:

modifying the sensor data to account for motion anomalies.

* * * * *